(12) United States Patent
Danielsen et al.

(10) Patent No.: US 10,519,432 B2
(45) Date of Patent: *Dec. 31, 2019

(54) XYLANASE VARIANTS AND POLYNUCLEOTIDES ENCODING SAME

(71) Applicant: Novozymes A/S, Bagsvaerd (DK)

(72) Inventors: Steffen Danielsen, Dyssegaard (DK); Peter Kamp Hansen, Lejre (DK); Frank Winther Rasmussen, Roskilde (DK); Roland Alexander Pache, Valby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/225,168

(22) Filed: Dec. 19, 2018

(65) Prior Publication Data

US 2019/0106689 A1    Apr. 11, 2019

Related U.S. Application Data

(62) Division of application No. 15/629,940, filed on Jun. 22, 2017, now Pat. No. 10,208,301.

(30) Foreign Application Priority Data

Jul. 8, 2016 (EP) .................................. 16178681

(51) Int. Cl.
```
C12N 1/20       (2006.01)
C12N 9/24       (2006.01)
C07H 21/04      (2006.01)
C12N 5/04       (2006.01)
C12N 15/87      (2006.01)
C12Q 1/68       (2018.01)
A01H 1/00       (2006.01)
```

(52) U.S. Cl.
CPC ............. *C12N 9/248* (2013.01); *C07H 21/04* (2013.01); *C12N 5/04* (2013.01); *C12N 9/2482* (2013.01); *C12N 15/87* (2013.01); *C12Q 1/68* (2013.01); *C12Y 302/01008* (2013.01); *A01H 1/00* (2013.01)

(58) Field of Classification Search
CPC ................................. C07H 21/04; C12N 5/04
USPC .......................................................... 435/219
See application file for complete search history.

(56) References Cited

U.S. PATENT DOCUMENTS

10,208,301 B2 * 2/2019 Danielsen .............. C07H 21/04
2016/0040203 A1 * 2/2016 St. John .................. C12P 19/14
                                                                   435/99

FOREIGN PATENT DOCUMENTS

WO    2003/106654 A2    12/2003
WO    2017/103159 A2     6/2017

OTHER PUBLICATIONS

Agger et al., J. Agric. Food Chem., vol. 58, pp. 6141-6148 (2010).
Crooks et al., EBI Accession No. BCM03676 (2016).
Crooks et al., EBI Accession No. BCM03682 (2016).
Huisman et al., Carbohydrate Polymers, vol. 43, pp. 269-279 (2000).
Nymand-Grarup et al., EBI Accession No. BEA26944 (2017).
Popper et al., Plant Physiology, vol. 153, pp. 373-383 (2010).
Shahi et al., Journal of Chemical and Pharmaceutical Research, vol. 8, No. 3, pp. 334-339 (2016).
Steer et al., EBI Accession No. ADJ35024 (2003).
John et al., Journal of Bacteriology, vol. 188, No. 24, pp. 8617-8626 (2006).
John et al., FEBS Letters, vol. 584, No. 21, pp. 4435-4441 (2010).
John et al., Acta Crystallographica Section D, vol. D70, pp. 2950-2958 (2014).
Steer et al., EBI Accession No. ADJ35026 (2003).

* cited by examiner

*Primary Examiner* — Tekchand Saidha
(74) *Attorney, Agent, or Firm* — Elias Lambiris

(57) ABSTRACT

The present invention relates to xylanase variants, polynucleotides encoding the variants; nucleic acid constructs, vectors, and host cells comprising the polynucleotides; compositions comprising the xylanase variants and methods of using the variants.

29 Claims, 1 Drawing Sheet

Specification includes a Sequence Listing.

Consensus (block 1):
AASDVTVNISAEKQVIRGFGGMNHPAWIGDLTAAQRETAFGNGQNLGFSILRIHVDENRNNWYRE Consensus (block 2):
VETAKSAIKHGAIVFASFWNPPSDMVETFN+NGDTSAKRLRYDKYAAYAQHLNDFVTFMKSNGVNL Consensus (block 3):
YAISVQNEPDYAHEWTWWTPQEILRFMRENAGSINGARVIAPESFQYLKNLSDPILNDPQALANMD Consensus (block 4):
ILGTHLYGTQVSDFPYPLFRQKGADKDLWMTEVYYPNSDNNSADRWPEALDVSQHIHNGMVEGDFQ Consensus (block 5):
AYVWWYIRRSYGPMKEDGTISKRGYNMAHFSKFVRPGYVRIDATKNPNPNVYVSAYKGDNKVVIVA Consensus (block 6):
INK+NTGVNQNFVLQNGSASQVSRWITSSSSNLQPGTNLKVTDNHFWAHLPAQSVTTFVV+R+

SEQUENCE LISTING

<160> NUMBER OF SEQ ID NOS: 6

<210> SEQ ID NO 1
<211> LENGTH: 391
<212> TYPE: PRT
<213> ORGANISM: Bacillus subtilis

<400> SEQUENCE: 1

```
Ala Ala Ser Asp Val Thr Val Asn Val Ser Ala Glu Lys Gln Val Ile
1               5                   10                  15

Arg Gly Phe Gly Gly Met Asn His Pro Ala Trp Ala Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Val Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Lys Tyr Asn Lys Tyr Ala
            100                 105                 110

Ala Tyr Ala Gln His Leu Asn Asp Phe Val Thr Phe Met Lys Asn Asn
        115                 120                 125

Gly Val Asn Leu Tyr Ala Ile Ser Val Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Thr Asn Ser Ala
225                 230                 235                 240

Asp Arg Trp Pro Glu Ala Leu Asp Val Ser Gln His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Ala Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335

Val Asn Gln Asn Phe Val Leu Gln Asn Gly Ser Ala Ser Asn Val Ser
            340                 345                 350

Arg Trp Ile Thr Ser Ser Ser Ser Asn Leu Gln Pro Gly Thr Asn Leu
        355                 360                 365
```

Thr Val Ser Gly Asn His Phe Trp Ala His Leu Pro Ala Gln Ser Val
370                 375                 380

Thr Thr Phe Val Val Asn Arg
385                 390

<210> SEQ ID NO 2
<211> LENGTH: 391
<212> TYPE: PRT
<213> ORGANISM: Bacillus amyloliquefaciens

<400> SEQUENCE: 2

Ala Ala Asn Asp Val Thr Val Asn Ile Ser Ala Glu Arg Gln Val Ile
1               5                   10                  15

Arg Gly Phe Gly Gly Met Asn His Pro Ala Trp Val Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
50                  55                  60

Lys Glu Val Glu Thr Ala Lys Ser Ala Ile Lys His Gly Ala Ile Val
65                  70                  75                  80

Phe Ala Ser Pro Trp Asn Pro Pro Asn Asp Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Asn Phe Met Lys Ser Asn
        115                 120                 125

Gly Val Asn Leu Tyr Ala Ile Ser Ile Gln Asn Glu Pro Asp Tyr Ala
130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Asp Val Ser Gln His Ile His Ser Ser
                245                 250                 255

Met Val Glu Gly Asp Leu Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
290                 295                 300

Asp Ala Thr Lys Asn Pro Asn Pro Asn Val Tyr Val Ser Ala Tyr Lys
305                 310                 315                 320

Gly Asp Asn Lys Val Val Ile Val Ala Ile Asn Lys Thr Asn Thr Gly
                325                 330                 335

Val Asn Gln Asn Phe Val Leu Gln Asn Gly Ser Ala Ser Gln Val Ser
            340                 345                 350

Arg Trp Ile Thr Ser Ser Asn Ser Asn Leu Gln Pro Gly Thr Asp Leu
            355                 360                 365

Lys Val Thr Asp Asn His Phe Trp Ala His Leu Pro Ala Gln Ser Val
370                 375                 380

Thr Thr Phe Val Val Lys Arg
385                 390

<210> SEQ ID NO 3
<211> LENGTH: 392
<212> TYPE: PRT
<213> ORGANISM: Bacillus licheniformis

<400> SEQUENCE: 3

Ala Ala Ser Asp Ala Thr Val Arg Leu Ser Ala Glu Lys Gln Val Ile
1               5                   10                  15

Arg Gly Phe Gly Gly Met Asn His Pro Ala Trp Ile Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Arg Glu Val Glu Thr Ala Lys Ser Ala Ile Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Arg Tyr Asp Lys Tyr Ala
            100                 105                 110

Ala Tyr Ala Lys His Leu Asn Asp Phe Val Thr Phe Met Lys Asn Asn
        115                 120                 125

Gly Val Asn Leu Tyr Ala Ile Ser Val Gln Asn Glu Pro Asp Tyr Ala
    130                 135                 140

His Asp Trp Thr Trp Trp Thr Pro Gln Glu Ile Leu Arg Phe Met Lys
145                 150                 155                 160

Glu Asn Ala Gly Ser Ile Asn Ala Arg Val Ile Ala Pro Glu Ser Phe
                165                 170                 175

Gln Tyr Leu Lys Asn Ile Ser Asp Pro Ile Val Asn Asp Pro Lys Ala
            180                 185                 190

Leu Ala Asn Met Asp Ile Leu Gly Ala His Leu Tyr Gly Thr Gln Leu
        195                 200                 205

Asn Asn Phe Ala Tyr Pro Leu Phe Lys Gln Lys Gly Ala Gly Lys Asp
    210                 215                 220

Leu Trp Met Thr Glu Val Tyr Tyr Pro Asn Ser Asp Asn His Ser Ala
225                 230                 235                 240

Asp Arg Trp Pro Glu Ala Leu Asp Val Ser His His Ile His Asn Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Val
    290                 295                 300

Asp Ala Thr Lys Ser Pro Ala Ser Asn Val Tyr Val Ser Ala Tyr Lys
305                 310                 315                 320

Gly Asp Asn Lys Val Val Ile Val Ala Ile Asn Lys Asn Asn Ser Gly
                325                 330                 335

Val Asn Gln Asn Phe Val Leu Gln Asn Gly Ser Val Ser Gln Val Ser
            340                 345                 350

Arg Trp Ile Thr Ser Ser Ser Asn Leu Gln Pro Gly Thr Asn Leu
        355                 360                 365

Asn Val Thr Asp Asn His Phe Trp Ala His Leu Pro Ala Gln Ser Val
        370                 375                 380

Thr Thr Phe Val Ala Asn Leu Arg
385                 390

<210> SEQ ID NO 4
<211> LENGTH: 391
<212> TYPE: PRT
<213> ORGANISM: Bacillus subtilis

<400> SEQUENCE: 4

Ala Ala Asn Asp Val Thr Val Asn Ile Ser Ala Glu Lys Gln Val Ile
1               5                   10                  15

Arg Gly Phe Gly Gly Met Asn His Pro Ala Trp Val Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Ile Lys His Gly Ala Ile Val
65                  70                  75                  80

Phe Ala Ser Pro Trp Asn Pro Pro Ser Asn Met Val Glu Thr Phe Asn
                85                  90                  95

His Asn Gly Asp Thr Ser Ala Lys Arg Leu Arg Tyr Asp Lys Tyr Ala
            100                 105                 110

Ala Tyr Ala Gln His Leu Asn Asp Phe Val Thr Phe Met Lys Ser Asn
        115                 120                 125

Gly Val Asn Leu Tyr Ala Ile Ser Ile Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Asn Asn Ser Ala
225                 230                 235                 240

Asp Arg Trp Pro Glu Ala Leu Asp Val Ser Gln His Ile His Asn Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Pro Asn Val Tyr Val Ser Ala Tyr Lys
305                 310                 315                 320

```
Gly Asp Asn Lys Val Ile Val Ala Ile Asn Lys Ser Asn Thr Gly
            325                 330                 335

Val Asn Gln Asn Phe Val Leu Gln Asn Gly Ser Ala Ser Gln Val Ser
        340                 345                 350

Arg Trp Ile Thr Ser Ser Asn Ser Asn Leu Gln Pro Gly Thr Asn Leu
            355                 360                 365

Lys Val Thr Asp Asn His Phe Trp Ala His Leu Pro Ala Gln Ser Val
370                 375                 380

Thr Thr Phe Val Val Ile Arg
385                 390
```

<210> SEQ ID NO 5
<211> LENGTH: 393
<212> TYPE: PRT
<213> ORGANISM: Paenibacillus pabuli

<400> SEQUENCE: 5

```
Ala Ala Ser Asp Val Thr Val Asn Leu Ser Ser Glu Lys Gln Leu Ile
1               5                   10                  15

Lys Gly Phe Gly Gly Ile Asn His Pro Asn Trp Ile Gly Asp Leu Thr
            20                  25                  30

Pro Ser Gln Arg Asp Thr Ala Phe Gly Asn Gly Gln Asn Gln Leu Gly
        35                  40                  45

Phe Ser Ile Leu Arg Ile Tyr Ile Asp Asp Asn Lys Asn Asn Trp Tyr
50                  55                  60

Lys Glu Ile Pro Thr Ala Lys Arg Ala Ile Glu Gln Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ala Ala Lys Arg Leu Lys Tyr Asp Lys Tyr Ala
            100                 105                 110

Ala Tyr Ala Gln His Leu Asn Asp Phe Val Ser Tyr Met Lys Ser Asn
        115                 120                 125

Gly Val Asn Leu Tyr Ala Ile Ser Val Gln Asn Glu Pro Asp Tyr Ala
130                 135                 140

His Asp Trp Thr Trp Trp Thr Pro Gln Glu Met Leu Arg Phe Met Lys
145                 150                 155                 160

Asp Tyr Ala Gly Ser Ile Thr Gly Thr Lys Val Met Ala Pro Glu Ser
                165                 170                 175

Phe Ser Tyr Leu Lys Glu Met Ser Asp Pro Ile Leu Asn Asp Pro Gln
            180                 185                 190

Ala Leu Ala Asn Met Asp Ile Leu Gly Ala His Thr Tyr Gly Thr Gln
        195                 200                 205

Phe Ser Asn Phe Pro Tyr Pro Leu Phe Lys Gln Lys Gly Ala Gly Lys
210                 215                 220

Glu Leu Trp Met Ser Glu Val Tyr Tyr Pro Asn Ser Asn Ala Asn Ser
225                 230                 235                 240

Ala Asp His Trp Pro Glu Ala Leu Asp Val Ser Tyr His Ile His His
                245                 250                 255

Ala Met Val Glu Ala Asp Phe Gln Ala Tyr Val Trp Trp Tyr Ile Arg
            260                 265                 270

Arg Gln Tyr Gly Pro Met Lys Glu Asp Gly Thr Ile Ser Lys Arg Gly
        275                 280                 285

Tyr Asn Met Ala His Phe Ser Lys Phe Val Arg Pro Gly Phe Val Arg
290                 295                 300
```

Val Asp Ala Thr Lys Asn Pro Asp Thr Gln Thr Phe Ile Ser Ala Phe
305                 310                 315                 320

Lys Gly Asp Asn Lys Val Val Ile Val Ala Ile Asn Arg Gly Thr Ser
                325                 330                 335

Ala Val Asn Gln Lys Phe Val Leu Gln Asn Gly Asn Ala Ser Asn Val
                340                 345                 350

Ser Ser Trp Val Thr Asp Ser Thr Arg Asn Leu Ala Ala Gly Ser Ser
        355                 360                 365

Ile Ile Met Thr Gly Asn Thr Phe Thr Ala Gln Leu Pro Ser Gln Ser
370                 375                 380

Val Thr Thr Phe Val Ala Gln Leu Asn
385                 390

<210> SEQ ID NO 6
<211> LENGTH: 391
<212> TYPE: PRT
<213> ORGANISM: Bacillus amyloliquefaciens

<400> SEQUENCE: 6

Ala Ala Ser Asp Ala Thr Val Asn Ile Ser Ala Glu Arg Gln Val Ile
1               5                   10                  15

Arg Gly Phe Gly Gly Met Asn His Pro Ala Trp Ile Gly Asp Leu Thr
                20                  25                  30

Ala Pro Gln Arg Val Thr Ala Phe Gly Asn Gly Gln Asn Gln Leu Gly
                35                  40                  45

Phe Ser Val Leu Arg Ile His Val Asp Glu Asn Arg Asn Asn Trp Tyr
    50                  55                  60

Lys Glu Val Glu Thr Ala Lys Ser Ala Ile Lys His Gly Ala Ile Val
65                  70                  75                  80

Phe Ala Ser Pro Trp Asn Pro Pro Asn Asp Met Val Glu Thr Phe Asn
                85                  90                  95

His Asn Gly Asp Thr Ser Ala Lys Arg Leu Arg Tyr Asp Lys Tyr Ala
                100                 105                 110

Ala Tyr Ala Gln His Leu Asn Asp Phe Val Asn Phe Met Lys Ser Asn
            115                 120                 125

Gly Val Asn Leu Tyr Ala Ile Ser Met Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Thr Arg Val Ile Ala Pro Glu Ser Phe
                165                 170                 175

Gln Tyr Leu Lys Asn Ile Ser Asp Pro Ile Leu Asn Asp Pro Gln Ala
            180                 185                 190

Leu Arg Asn Met Asp Ile Leu Gly Thr His Leu Tyr Gly Thr Gln Val
        195                 200                 205

Ser Gln Phe Pro Tyr Pro Leu Phe Lys Gln Lys Gly Gly Gly Lys Glu
    210                 215                 220

Leu Trp Met Thr Glu Val Tyr Tyr Pro Asn Ser Asp Asn Tyr Ser Ala
225                 230                 235                 240

Asp Arg Trp Pro Glu Ala Leu Gly Val Ser Glu His Ile His His Ser
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Met Ile Ser Lys Arg Gly Tyr
    275                 280                 285

-continued

```
Asn Met Ala His Phe Ser Lys Phe Val Arg Pro Gly Tyr Val Arg Ile
    290             295             300

Asp Ala Thr Lys Asn Pro Glu Pro Asn Val Tyr Val Ser Ala Tyr Lys
305             310             315             320

Gly Asp Asn Lys Val Val Ile Val Ala Ile Asn Lys Asn Asn Thr Gly
            325             330             335

Val Asn Gln Asn Phe Val Leu Gln Asn Gly Thr Ala Ser Gln Val Ser
            340             345             350

Arg Trp Ile Thr Ser Ser Ser Ser Asn Leu Gln Pro Gly Thr Asp Leu
        355             360             365

Lys Val Thr Asp Asn His Phe Trp Ala His Leu Pro Ala Gln Ser Val
    370             375             380

Thr Thr Phe Val Val Lys Arg
385             390
```

XYLANASE VARIANTS AND POLYNUCLEOTIDES ENCODING SAME

CROSS-REFERENCE TO RELATED APPLICATIONS

This application is divisional of U.S. application Ser. No. 15/629,940 filed on Jun. 22, 2017, now U.S. Pat. No. 10,208,301, which claims priority or the benefit under 35 U.S.C. 119 of European application no. 16178681.9 filed Jul. 8, 2016. The content of these applications is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to xylanase variants, polynucleotides encoding the variants; nucleic acid constructs, vectors, and host cells comprising the polynucleotides; compositions comprising the xylanase variants and methods of using the variants.

Description of the Related Art

Xylans are hemicelluloses found in all land plants (Popper and Tuohy, 2010, *Plant Physiology* 153: 373-383). They are especially abundant in secondary cell walls and xylem cells. In grasses, with type II cell walls, glucurono arabinoxylans are the main hemicellulose and are present as soluble or insoluble dietary fiber in many grass based food and feed products.

Plant xylans have a β-1,4-linked xylopyranose backbone that can be substituted at the O2 or O3 position with arabinose, glucuronic acid and acetic acid in a species and tissue specific manner. The starch-rich seeds of the subfamily Panicoideae with economically important species such as corn, *sorghum*, rice and millet have special types of highly substituted xylans in their cell walls. Compared to wheat flour, wherein over 60% of the xylosyl units in the arabinoxylan backbone are unsubstituted. In corn kernel xylan, the corresponding percentage of unsubstituted backbone xylosyls is 20-30%, and in *sorghum* it is 35-40% (Huismann et al., 2000, *Carbohydrate Polymers* 42: 269-279). Furthermore, in corn and *sorghum* the xylan side chains can be longer than a single arabinose or glucuronic acid substitution which is common in other xylans. This added side chain complexity is often due to L- and D-galactose and D-xylose sugars bound to the side chain arabinose or glucuronic acid. About every tenth arabinose in corn kernel xylan is also esterified with a ferulic acid and about every fourth xylose carries an acetylation (Agger et al., 2010, *J. Agric. Food Chem.* 58: 6141-6148). All of these factors combined make the highly substituted xylans in corn and *sorghum* resistant to degradation by traditional xylanases.

The known enzymes responsible for the hydrolysis of the xylan backbone are classified into enzyme families based on sequence similarity (cazy.org). The enzymes with mainly endo-xylanase activity have previously been described in Glycoside hydrolase (GH) families 5, 8, 10, 11, 30 and 98. The enzymes within a family share some characteristics such as 3D fold and they usually share the same reaction mechanism. Some GH families have narrow or mono-specific substrate specificities while other families have broad substrate specificities.

Commercially available GH10 and GH11 xylanases are often used to break down the xylose backbone of arabinoxylan. In animal feed this results in a degradation of the cereal cell wall with a subsequent improvement in nutrient release (starch and protein) encapsulated within the cells. Degradation of xylan also results in the formation of xylose oligomers that may be utilised for hind gut fermentation and therefore can help an animal to obtain more digestible energy. However, such xylanases are sensitive to side chain steric hindrance and whilst they are effective at degrading arabinoxylan from wheat, they are not very effective on the xylan found in the seeds of Poaceae species, such as corn or *sorghum*.

Corn is used around the world in animal feed and thus there is a need to discover new polypeptides having xylanase activity that are capable of breaking down the highly branched xylan backbone in the cell wall in order to release more xylose and other nutrients which are trapped inside the cell wall.

The present invention provides xylanase variants with improved properties compared to its parent.

SUMMARY OF THE INVENTION

The present invention relates to xylanase variants, comprising a substitution at one or more (e.g., several) positions corresponding to positions 24, 26, 36, 37, 60, 71, 74, 75, 76, 124, 133, 155, 167, 208, 317, and 321 of SEQ ID NO: 1, wherein the xylanase variant has xylanase activity and wherein the xylanase variant has at least 60% sequence identity to SEQ ID NO: 1, 2, 3, 4, 5 or 6. The invention also relates to compositions, such as granules, liquid compositions, animal feed additives or animal feed comprising the xylanase variant of the invention.

The present invention also relates to isolated polynucleotides encoding the xylanase variants; nucleic acid constructs, vectors, and host cells comprising the polynucleotides; and methods of producing the xylanase variants.

The present invention further relates to the use of the xylanase variants in animal feed; in animal feed additives; in the preparation of a composition for use in animal feed; for improving the nutritional value of an animal feed; for increasing digestibility of an animal feed; for improving one or more performance parameters in an animal; for solubilizing xylan from plant based material; and/or for releasing starch from plant based material; processes for producing a fermentation product; methods for preparing a dough or a baked product; and methods for obtaining a xylanase variant.

Overview of Sequence Listing

SEQ ID NO: 1 is the amino acid sequence of a mature GH30 xylanase from *Bacillus subtilis*.

SEQ ID NO: 2 is the amino acid sequence of a mature GH30 xylanase from *Bacillus amyloliquefaciens*.

SEQ ID NO: 3 is the amino acid sequence of a mature GH30 xylanase from *Bacillus licheniformis*.

SEQ ID NO: 4 is the amino acid sequence of a mature GH30 xylanase from *Bacillus subtilis*.

SEQ ID NO: 5 is the amino acid sequence of a mature GH30 xylanase from *Paenibacillus pabuli*.

SEQ ID NO: 6 is the amino acid sequence of a mature GH30 xylanase from *Bacillus amyloliquefaciens* HB-26.

BRIEF DESCRIPTION OF THE FIGURES

FIG. 1 is an alignment of the amino acid sequences of a *Bacillus subtilis* xylanase (SEQ ID NO: 1), a *Bacillus amyloliquefaciens* xylanase (SEQ ID NO: 2), a *Bacillus licheniformis* xylanase (SEQ ID NO: 3), a *Bacillus subtilis* xylanase (SEQ ID NO: 4), a *Paenibacillus pabuli* xylanase (SEQ ID NO: 5) and a *Bacillus amyloliquefaciens* xylanase (SEQ ID NO: 6).

DEFINITIONS

Xylanase: The term "xylanase" means a glucuronoarabinoxylan endo-1,4-beta-xylanase (E.C. 3.2.1.136) that catalyses the endohydrolysis of 1,4-beta-D-xylosyl links in some glucuronoarabinoxylans. Xylanase activity can be determined with 0.2% AZCL-glucuronoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-glucuronoxylan as substrate in 200 mM sodium phosphate pH 6.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Animal: The term "animal" refers to all animals except humans. Examples of animals are non-ruminants, and ruminants. Ruminant animals include, for example, animals such as sheep, goats, cattle, e.g., beef cattle, cows, and young calves, deer, yank, camel, llama and kangaroo. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Arabinoxylan-containing material: The term "Arabinoxylan-containing material" means any material containing arabinoxylan. Arabinoxylan is a hemicellulose found in both the primary and secondary cell walls of plants, including woods and cereal grains, consisting of copolymers of two pentose sugars, arabinose and xylose. The arabinoxylan chain contains a large number of 1,4-linked xylose units. Many xylose units are substituted with 2-, 3- or 2,3-substituted arabinose residues.

Examples of arabinoxylan-containing material are forage, roughage, seeds and grains (either whole or prepared by crushing, milling, etc from, e.g., corn, oats, rye, barley, wheat), trees or hard woods (such as poplar, willow, *eucalyptus*, palm, maple, birch), bamboo, herbaceous and/or woody energy crops, agricultural food and feed crops, animal feed products, cassava peels, cocoa pods, sugar cane, sugar beet, locust bean pulp, vegetable or fruit pomaces, wood waste, bark, shavings, sawdust, wood pulp, pulping liquor, waste paper, cardboard, construction and demolition wood waste, industrial or municipal waste water solids or sludge, manure, by-product from brewing and/or fermentation processes, wet distillers grain, dried distillers grain, spent grain, vinasse and bagasse.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (Lucerne), birdsfoot trefoil, *brassica* (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, *miscanthus*, orchard grass, ryegrass, switchgrass, Timothy-grass), corn (maize), hemp, millet, barley, oats, rye, *sorghum*, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Preferred sources of arabinoxylan-containing materials are forage, roughage, seeds and grains, sugar cane, sugar beet and wood pulp.

Body Weight Gain: The term "body weight gain" means an increase in live weight of an animal during a given period of time, e.g., the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide; wherein the fragment has xylanase activity. In one aspect, a fragment comprises at least 330 amino acid residues, at least 350 amino acid residues, or at least 370 amino acid residues.

In one aspect, a fragment comprises at least 330 amino acid residues of SEQ ID NO: 1, at least 350 amino acid residues of SEQ ID NO: 1, or at least 370 amino acid residues of SEQ ID NO: 1. In one aspect, a fragment comprises at least 330 amino acid residues of SEQ ID NO: 2, at least 350 amino acid residues of SEQ ID NO: 2, or at least 370 amino acid residues of SEQ ID NO: 2. In one aspect, a fragment comprises at least 330 amino acid residues of SEQ ID NO: 3, at least 350 amino acid residues of SEQ ID NO: 3, or at least 370 amino acid residues of SEQ ID NO: 3. In one aspect, a fragment comprises at least 330 amino acid residues of SEQ ID NO: 4, at least 350 amino acid residues of SEQ ID NO: 4, or at least 370 amino acid residues of SEQ ID NO: 4. In one aspect, a fragment comprises at least 330 amino acid residues of SEQ ID NO: 5, at least 350 amino acid residues of SEQ ID NO: 5, or at least 370 amino acid residues of SEQ ID NO: 5. In one aspect, a fragment comprises at least 330 amino acid residues of SEQ ID NO: 6, at least 350 amino acid residues of SEQ ID NO: 6, or at least 370 amino acid residues of SEQ ID NO: 6.

Highly branched xylan: The term "highly branched xylan" means that more than 50% of xylosyl units in the arabinoxylan backbone are substituted. This is preferably calculated from linkage analysis as performed in Huismann et al., 2000, *Carbohydrate Polymers* 42:269-279.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability. In an embodiment, the improved property is improved thermostability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 391 of SEQ ID NO: 1. In one aspect, the mature polypeptide is amino acids 1 to 391 of SEQ ID NO: 2. In one aspect, the mature polypeptide is amino acids 1 to 392 of SEQ ID NO: 3. In one aspect, the mature polypeptide is amino acids 1 to 391 of SEQ ID NO: 4. In one aspect, the mature polypeptide is amino acids 1 to 393 of SEQ ID NO: 5. In one aspect, the mature polypeptide is amino acids 1 to 391 of SEQ ID NO: 6.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having xylanase activity.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g., the small intestine. Nutrient digestibility may be measured as the difference between what is administered to the subject and what. comes out in the faeces of the subject, or between what is administered to the subject and what remains in the digesta on a specified segment of the gastro intestinal tract, e.g., the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g., the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Parent or parent xylanase: The term "parent" or "parent xylanase" means a xylanase to which a substitution is made to produce the xylanase variants of the present invention. The parent may be a naturally occurring (wild-type) polypeptide or a variant or fragment thereof.

Percentage solubilized xylan: The term "percentage solubilized xylan" means the amount of xylose measured in the supernatant after incubation with an enzyme compared to the total amount of xylose present in the substrate before the incubation with the enzyme. For the purpose of the present invention, the percentage solubilized xylan may be calculated using defatted destarched maize (DFDSM) as substrate. DFDSM is prepared according to 'Preparation of Defatted Destarched Maize (DFDSM)' in the experimental section.

The percentage solubilized xylan from defatted destarched maize (DFDSM) may be determined using the reaction conditions 20 µg enzyme/g DFDSM and incubation at 40° C., pH 5 for 2.5 hours as described in the 'Xylose solubilization assay' herein. Thus the term 'is performed under the reaction conditions 20 µg xylanase variant per gram defatted destarched maize (DFDSM) and incubation at 40° C., pH 5 for 2.5 hours' is to be understood that the percentage solubilised xylan is calculated as described in the 'Xylose solubilization assay' herein.

In a more detailed embodiment, 2% (w/w) DFDSM suspension was prepared in 100 mM sodium acetate, 5 mM $CaCl_2$, pH 5 and allowed to hydrate for 30 min at room temperature under gently stirring. After hydration, 200 µl substrate suspension was pipetted into a 96 well plate and mixed with 20 µl enzyme solution to obtain a final enzyme concentration of 20 PPM relative to substrate (20 µg enzyme/g substrate). The enzyme/substrate mixtures were left for hydrolysis in 2.5 h at 40° C. under gently agitation (500 RPM) in a plate incubator. After enzymatic hydrolysis, the enzyme/substrate plates were centrifuged for 10 min at 3000 RPM and 50 µl supernatant was mixed with 100 µl 1.6 M HCl and transferred to 300 µl PCR tubes and left for acid hydrolysis for 40 min at 90° C. in a PCR machine. Samples were neutralized with 125 µl 1.4 M NaOH after acid hydrolysis and loaded on the HPAE-PAD for mono-saccharide analysis.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), e.g., version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), e.g., version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment–Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.4×SSC, 0.2% SDS at 55° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.4×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1.4×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.7×SSC, 0.2% SDS at 65° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.7×SSC, 0.2% SDS at 70° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.7×SSC, 0.2% SDS at 75° C.

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the xylanase activity of the polypeptide of SEQ ID NO: 1.

Wild-type xylanase: The term "wild-type" xylanase means a xylanase expressed by a naturally occurring microorganism, such as a bacterium, yeast, or filamentous fungus found in nature.

Conventions for Designation of Variants

For purposes of the present invention, SEQ ID NO: 1 is used to determine the corresponding amino acid residue in another xylanase. The amino acid sequence of another xylanase is aligned with SEQ ID NO: 1, and based on the alignment, the amino acid position number corresponding to any amino acid residue in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), e.g., version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another xylanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1794), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTH READER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by a plus sign ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated xylanase variants, comprising a substitution at one or more (e.g., several) positions corresponding to positions 24, 26, 36, 37, 60, 71, 74, 75, 76, 124, 133, 155, 167, 208, 317, and 321 of SEQ ID NO: 1, wherein the variant has xylanase activity.

Variants

The present invention provides xylanase variants, comprising a substitution at one or more (e.g., several) positions corresponding to positions 24, 26, 36, 37, 60, 71, 74, 75, 76, 124, 133, 155, 167, 208, 317, and 321, wherein the variant has xylanase activity. In an embodiment, the variant has improved thermostability compared to the parent xylanase. In an embodiment, the variants are GH30 xylanase variants, preferably GH30 subfamily 8 variants.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent xylanase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 1. In an embodiment, the variant has improved thermostability compared to SEQ ID NO: 1.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 2. In an embodiment, the variant has improved thermostability compared to SEQ ID NO: 2.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 3. In an embodiment, the variant has improved thermostability compared to SEQ ID NO: 3.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 4. In an embodiment, the variant has improved thermostability compared to SEQ ID NO: 4.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 5. In an embodiment, the variant has improved thermostability compared to SEQ ID NO: 5.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to SEQ ID NO: 6. In an embodiment, the variant has improved thermostability compared to SEQ ID NO: 6.

In one embodiment, the invention relates to a GH30 subfamily 8 xylanase variant having improved thermostability compared to the parent xylanase, comprising a substitution at one or more (e.g., several) positions selected from the group consisting of 24, 26, 36, 37, 60, 71, 74, 75, 76, 124, 133, 155, 167, 208, 317, and 321, wherein the positions correspond to the positions of SEQ ID NO: 1 and wherein the variant has xylanase activity and has at least 70% identity, preferably at least 80%, more preferably at least 85%, even more preferably at least 90%, or most preferably at least 95% identity to SEQ ID NO: 1.

In an embodiment, the parent xylanase is a *Bacillus* GH30 subfamily 8 xylanase, such as described below herein. In one embodiment, the parent xylanase is a *Bacillus subtilis* GH30 subfamily 8 xylanase, such as SEQ ID NO: 1 or SEQ ID NO: 4, preferably SEQ ID NO: 1. In one embodiment, the parent xylanase is a *Bacillus amyloliquefaciens* GH30 subfamily 8 xylanase, such as SEQ ID NO: 2 or SEQ ID NO: 6. In one embodiment, the parent xylanase is a *Bacillus licheniformis* GH30 subfamily 8 xylanase, such as SEQ ID NO: 3. In another aspect, the parent xylanase is a *Paenibacillus* GH30 subfamily 8 xylanase, such as described below herein. In one embodiment, the parent xylanase is a *Paenibacillus pabuli* GH30 subfamily 8 xylanase, such as SEQ ID NO: 5.

In one aspect, the number of alterations in the variants of the present invention is 1-20, e.g., 1-10 and 1-5, such as 1, 2, 3, 4, 5, 6, 7, 8, 9 or 10 alterations.

In another aspect, a variant comprises a substitution at one or more (e.g., several) positions corresponding to positions 24, 26, 36, 37, 60, 71, 74, 75, 76, 124, 133, 155, 167, 208, 317, and 321. In another aspect, a variant comprises a substitution at two positions corresponding to any of positions 24, 26, 36, 37, 60, 71, 74, 75, 76, 124, 133, 155, 167, 208, 317, and 321. In another aspect, a variant comprises a substitution at three positions corresponding to any of positions 24, 26, 36, 37, 60, 71, 74, 75, 76, 124, 133, 155, 167, 208, 317, and 321. In another aspect, a variant comprises a substitution at each position corresponding to positions 24, 26, 36, 37, 60, 71, 74, 75, 76, 124, 133, 155, 167, 208, 317, and 321. In an embodiment, the variant has improved thermostability compared to the parent xylanase. In an embodiment, the parent xylanase is a *Bacillus* GH30 subfamily 8 xylanase, such as described below herein. In one embodiment, the parent xylanase is a *Bacillus subtilis* GH30 subfamily 8 xylanase, such as SEQ ID NO: 1 or SEQ ID NO: 4, preferably SEQ ID NO: 1. In one embodiment, the parent xylanase is a *Bacillus amyloliquefaciens* GH30 subfamily 8 xylanase, such as SEQ ID NO: 2 or SEQ ID NO: 6. In one embodiment, the parent xylanase is a *Bacillus licheniformis* GH30 subfamily 8 xylanase, such as SEQ ID NO: 3. In another aspect, the parent xylanase is a *Paenibacillus* GH30 subfamily 8 xylanase, such as described below herein. In one embodiment, the parent xylanase is a *Paenibacillus pabuli* GH30 subfamily 8 xylanase, such as SEQ ID NO: 5.

In another aspect, the variant comprises or consists of a substitution at a position corresponding to position 24. In another aspect, the amino acid at a position corresponding to position 24 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Trp. In another aspect, the variant comprises or consists of the substitution H24W of the polypeptide of SEQ ID NO: 1.

In another aspect, the variant comprises or consists of a substitution at a position corresponding to position 26. In another aspect, the amino acid at a position corresponding to position 26 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Glu. In another aspect, the variant comprises or consists of the substitution A26E of the polypeptide of SEQ ID NO: 1.

In another aspect, the variant comprises or consists of a substitution at a position corresponding to position 36. In another aspect, the amino acid at a position corresponding to position 36 is substituted with Ala, Asn, Arg, Asp, Cys, Gln, Glu, Gly, His, Ile, Leu, Lys, Met, Phe, Pro, Ser, Thr, Trp, Tyr, or Val, in particular, with Leu or Thr. In another aspect, the variant comprises or consists of the substitution R36L,T of the polypeptide of SEQ ID NO: 1.

In another aspect, the variant comprises or consists of a substitution at a position corresponding to position 37. In another aspect, the amino acid at a position corresponding to position 37 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Leu or Thr. In another aspect, the variant comprises or consists of the substitution E37L,T of the polypeptide of SEQ ID NO: 1.

In another aspect, the variant comprises or consists of a substitution at a position corresponding to position 60. In another aspect, the amino acid at a position corresponding to position 60 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Asn. In another aspect, the variant comprises or consists of the substitution R60N of the polypeptide of SEQ ID NO: 1.

In another aspect, the variant comprises or consists of a substitution at a position corresponding to position 71. In another aspect, the amino acid at a position corresponding to position 71 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Ile, Leu, or Thr. In another aspect, the variant comprises or consists of the substitution K71I,L,T of the polypeptide of SEQ ID NO: 1.

In another aspect, the variant comprises or consists of a substitution at a position corresponding to position 74. In another aspect, the amino acid at a position corresponding to position 74 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Ile or Leu. In another aspect, the variant comprises or consists of the substitution V74I,L of the polypeptide of SEQ ID NO: 1.

In another aspect, the variant comprises or consists of a substitution at a position corresponding to position 75. In another aspect, the amino acid at a position corresponding to position 75 is substituted with Ala, Arg, Asn, Asp, Cys, Gin, Glu, Gly, His, Ile, Leu, Lys, Met, Phe, Pro, Ser, Thr, Trp, Tyr, or Val, in particular, with Asn, Glu, Leu, or Thr. In another aspect, the variant comprises or consists of the substitution K75E,L,N,T of the polypeptide of SEQ ID NO: 1.

In another aspect, the variant comprises or consists of a substitution at a position corresponding to position 76. In another aspect, the amino acid at a position corresponding to position 76 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Leu. In another aspect, the variant comprises or consists of the substitution H76L of the polypeptide of SEQ ID NO: 1.

In another aspect, the variant comprises or consists of a substitution at a position corresponding to position 124. In another aspect, the amino acid at a position corresponding to position 124 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Tyr. In another aspect, the variant comprises or consists of the substitution F124Y of the polypeptide of SEQ ID NO: 1.

In another aspect, the variant comprises or consists of a substitution at a position corresponding to position 133. In another aspect, the amino acid at a position corresponding to position 133 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Ile. In another aspect, the variant comprises or consists of the substitution Y133I of the polypeptide of SEQ ID NO: 1.

In another aspect, the variant comprises or consists of a substitution at a position corresponding to position 155. In another aspect, the amino acid at a position corresponding to position 155 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Met. In another aspect, the variant comprises or consists of the substitution I155M of the polypeptide of SEQ ID NO: 1.

In another aspect, the variant comprises or consists of a substitution at a position corresponding to position 167. In another aspect, the amino acid at a position corresponding to position 167 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Glu. In another aspect, the variant comprises or consists of the substitution N167E of the polypeptide of SEQ ID NO: 1.

In another aspect, the variant comprises or consists of a substitution at a position corresponding to position 208. In another aspect, the amino acid at a position corresponding to position 208 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Leu. In another aspect, the variant comprises or consists of the substitution V208L of the polypeptide of SEQ ID NO: 1.

In another aspect, the variant comprises or consists of a substitution at a position corresponding to position 317. In another aspect, the amino acid at a position corresponding to position 317 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Asp. In another aspect, the variant comprises or consists of the substitution S317D of the polypeptide of SEQ ID NO: 1.

In another aspect, the variant comprises or consists of a substitution at a position corresponding to position 321. In another aspect, the amino acid at a position corresponding to position 321 is substituted with Ala, Arg, Asn, Asp, Cys, Gln, Glu, Gly, His, Ile, Leu, Lys, Met, Phe, Pro, Ser, Thr, Trp, Tyr, or Val, in particular, with Ala. In another aspect, the variant comprises or consists of the substitution G321A of the polypeptide of SEQ ID NO: 1.

In another aspect, the variant comprises or consists of substitutions at positions corresponding to positions 24 and 26, such as those described above.

In another aspect, the variant comprises or consists of substitutions at positions corresponding to positions 24 and 60, such as those described above.

In another aspect, the variant comprises or consists of substitutions at positions corresponding to positions 24 and 71, such as those described above.

In another aspect, the variant comprises or consists of substitutions at positions corresponding to positions 24 and 74, such as those described above.

In another aspect, the variant comprises or consists of substitutions at positions corresponding to positions 24 and 75, such as those described above.

In another aspect, the variant comprises or consists of substitutions at positions corresponding to positions 24 and 76, such as those described above.

In another aspect, the variant comprises or consists of substitutions at positions corresponding to positions 24 and 155, such as those described above.

In another aspect, the variant comprises or consists of substitutions at positions corresponding to positions 24 and 208, such as those described above.

In another aspect, the variant comprises or consists of substitutions at positions corresponding to positions 24 and 317, such as those described above.

In another aspect, the variant comprises or consists of substitutions at positions corresponding to positions 24 and 321, such as those described above.

In another aspect, the variant comprises or consists of substitutions at positions corresponding to positions 26 and 60, such as those described above.

In another aspect, the variant comprises or consists of substitutions at positions corresponding to positions 26 and 71, such as those described above.

In another aspect, the variant comprises or consists of substitutions at positions corresponding to positions 26 and 74, such as those described above.

In another aspect, the variant comprises or consists of substitutions at positions corresponding to positions 26 and 75, such as those described above.

In another aspect, the variant comprises or consists of substitutions at positions corresponding to positions 26 and 76, such as those described above.

In another aspect, the variant comprises or consists of substitutions at positions corresponding to positions 26 and 155, such as those described above.

In another aspect, the variant comprises or consists of substitutions at positions corresponding to positions 26 and 208, such as those described above.

In another aspect, the variant comprises or consists of substitutions at positions corresponding to positions 26 and 317, such as those described above.

In another aspect, the variant comprises or consists of substitutions at positions corresponding to positions 26 and 321, such as those described above.

In another aspect, the variant comprises or consists of substitutions at positions corresponding to positions 36 and 37, such as those described above.

In another aspect, the variant comprises or consists of substitutions at positions corresponding to positions 36 and 155, such as those described above.

In another aspect, the variant comprises or consists of substitutions at positions corresponding to positions 36 and 208, such as those described above.

In another aspect, the variant comprises or consists of substitutions at positions corresponding to positions 37 and 155, such as those described above.

In another aspect, the variant comprises or consists of substitutions at positions corresponding to positions 37 and 208, such as those described above.

In another aspect, the variant comprises or consists of substitutions at positions corresponding to positions 37 and 317, such as those described above.

In another aspect, the variant comprises or consists of substitutions at positions corresponding to positions 37 and 321, such as those described above.

In another aspect, the variant comprises or consists of substitutions at positions corresponding to positions 71 and 74, such as those described above.

In another aspect, the variant comprises or consists of substitutions at positions corresponding to positions 71 and 75, such as those described above.

In another aspect, the variant comprises or consists of substitutions at positions corresponding to positions 71 and 76, such as those described above.

In another aspect, the variant comprises or consists of substitutions at positions corresponding to positions 71 and 155, such as those described above.

In another aspect, the variant comprises or consists of substitutions at positions corresponding to positions 71 and 208, such as those described above.

In another aspect, the variant comprises or consists of substitutions at positions corresponding to positions 71 and 317, such as those described above.

In another aspect, the variant comprises or consists of substitutions at positions corresponding to positions 71 and 321, such as those described above.

In another aspect, the variant comprises or consists of substitutions at positions corresponding to positions 74 and 75, such as those described above.

In another aspect, the variant comprises or consists of substitutions at positions corresponding to positions 74 and 76, such as those described above.

In another aspect, the variant comprises or consists of substitutions at positions corresponding to positions 74 and 155, such as those described above.

In another aspect, the variant comprises or consists of substitutions at positions corresponding to positions 74 and 208, such as those described above.

In another aspect, the variant comprises or consists of substitutions at positions corresponding to positions 74 and 317, such as those described above.

In another aspect, the variant comprises or consists of substitutions at positions corresponding to positions 74 and 321, such as those described above.

In another aspect, the variant comprises or consists of substitutions at positions corresponding to positions 75 and 76, such as those described above.

In another aspect, the variant comprises or consists of substitutions at positions corresponding to positions 75 and 155, such as those described above.

In another aspect, the variant comprises or consists of substitutions at positions corresponding to positions 75 and 208, such as those described above.

In another aspect, the variant comprises or consists of substitutions at positions corresponding to positions 75 and 317, such as those described above.

In another aspect, the variant comprises or consists of substitutions at positions corresponding to positions 75 and 321, such as those described above.

In another aspect, the variant comprises or consists of substitutions at positions corresponding to positions 76 and 155, such as those described above.

In another aspect, the variant comprises or consists of substitutions at positions corresponding to positions 76 and 208, such as those described above.

In another aspect, the variant comprises or consists of substitutions at positions corresponding to positions 76 and 317, such as those described above.

In another aspect, the variant comprises or consists of substitutions at positions corresponding to positions 76 and 321, such as those described above.

In another aspect, the variant comprises or consists of substitutions at positions corresponding to positions 124 and 155, such as those described above.

In another aspect, the variant comprises or consists of substitutions at positions corresponding to positions 124 and 208, such as those described above.

In another aspect, the variant comprises or consists of substitutions at positions corresponding to positions 124 and 317, such as those described above.

In another aspect, the variant comprises or consists of substitutions at positions corresponding to positions 124 and 321, such as those described above.

In another aspect, the variant comprises or consists of substitutions at positions corresponding to positions 133 and 155, such as those described above.

In another aspect, the variant comprises or consists of substitutions at positions corresponding to positions 133 and 208, such as those described above.

In another aspect, the variant comprises or consists of substitutions at positions corresponding to positions 133 and 317, such as those described above.

In another aspect, the variant comprises or consists of substitutions at positions corresponding to positions 133 and 321, such as those described above.

In another aspect, the variant comprises or consists of substitutions at positions corresponding to positions 155 and 167, such as those described above.

In another aspect, the variant comprises or consists of substitutions at positions corresponding to positions 155 and 208, such as those described above.

In another aspect, the variant comprises or consists of substitutions at positions corresponding to positions 155 and 317, such as those described above.

In another aspect, the variant comprises or consists of substitutions at positions corresponding to positions 155 and 321, such as those described above.

In another aspect, the variant comprises or consists of substitutions at positions corresponding to positions 167 and 208, such as those described above.

In another aspect, the variant comprises or consists of substitutions at positions corresponding to positions 167 and 317, such as those described above.

In another aspect, the variant comprises or consists of substitutions at positions corresponding to positions 167 and 321, such as those described above.

In another aspect, the variant comprises or consists of substitutions at positions corresponding to positions 208 and 317, such as those described above.

In another aspect, the variant comprises or consists of substitutions at positions corresponding to positions 208 and 321, such as those described above.

In another aspect, the variant comprises or consists of substitutions at positions corresponding to positions 317 and 321, such as those described above.

In another aspect, the variant comprises or consists of substitutions at positions corresponding to positions 24, 26, and 71, such as those described above.

In another aspect, the variant comprises or consists of substitutions at positions corresponding to positions 24, 26, and 74, such as those described above.

In another aspect, the variant comprises or consists of substitutions at positions corresponding to positions 24, 26, and 75, such as those described above.

In another aspect, the variant comprises or consists of substitutions at positions corresponding to positions 24, 26, and 76, such as those described above.

In another aspect, the variant comprises or consists of substitutions at positions corresponding to positions 24, 26, and 155, such as those described above.

In another aspect, the variant comprises or consists of substitutions at positions corresponding to positions 24, 26, and 208, such as those described above.

In another aspect, the variant comprises or consists of substitutions at positions corresponding to positions 24, 71, and 74, such as those described above.

In another aspect, the variant comprises or consists of substitutions at positions corresponding to positions 24, 71, and 75, such as those described above.

In another aspect, the variant comprises or consists of substitutions at positions corresponding to positions 24, 71, and 76, such as those described above.

In another aspect, the variant comprises or consists of substitutions at positions corresponding to positions 24, 71, and 155, such as those described above.

In another aspect, the variant comprises or consists of substitutions at positions corresponding to positions 24, 71, and 208, such as those described above.

In another aspect, the variant comprises or consists of substitutions at positions corresponding to positions 24, 74, and 75, such as those described above.

In another aspect, the variant comprises or consists of substitutions at positions corresponding to positions 24, 74, and 76, such as those described above.

In another aspect, the variant comprises or consists of substitutions at positions corresponding to positions 24, 74, and 155, such as those described above.

In another aspect, the variant comprises or consists of substitutions at positions corresponding to positions 24, 74, and 208, such as those described above.

In another aspect, the variant comprises or consists of substitutions at positions corresponding to positions 24, 75, and 76, such as those described above.

In another aspect, the variant comprises or consists of substitutions at positions corresponding to positions 24, 75, and 155, such as those described above.

In another aspect, the variant comprises or consists of substitutions at positions corresponding to positions 24, 75, and 208, such as those described above.

In another aspect, the variant comprises or consists of substitutions at positions corresponding to positions 24, 76, and 155, such as those described above.

In another aspect, the variant comprises or consists of substitutions at positions corresponding to positions 24, 76, and 208, such as those described above.

In another aspect, the variant comprises or consists of substitutions at positions corresponding to positions 24, 155, and 208, such as those described above.

In another aspect, the variant comprises or consists of substitutions at positions corresponding to positions 26, 71, and 74, such as those described above.

In another aspect, the variant comprises or consists of substitutions at positions corresponding to positions 26, 71, and 75, such as those described above.

In another aspect, the variant comprises or consists of substitutions at positions corresponding to positions 26, 71, and 76, such as those described above.

In another aspect, the variant comprises or consists of substitutions at positions corresponding to positions 26, 71, and 155, such as those described above.

In another aspect, the variant comprises or consists of substitutions at positions corresponding to positions 26, 71, and 208, such as those described above.

In another aspect, the variant comprises or consists of substitutions at positions corresponding to positions 26, 74, and 75, such as those described above.

In another aspect, the variant comprises or consists of substitutions at positions corresponding to positions 26, 74, and 76, such as those described above.

In another aspect, the variant comprises or consists of substitutions at positions corresponding to positions 26, 74, and 155, such as those described above.

In another aspect, the variant comprises or consists of substitutions at positions corresponding to positions 26, 74, and 208, such as those described above.

In another aspect, the variant comprises or consists of substitutions at positions corresponding to positions 26, 75, and 76, such as those described above.

In another aspect, the variant comprises or consists of substitutions at positions corresponding to positions 26, 75, and 155, such as those described above.

In another aspect, the variant comprises or consists of substitutions at positions corresponding to positions 26, 75, and 208, such as those described above.

In another aspect, the variant comprises or consists of substitutions at positions corresponding to positions 26, 76, and 155, such as those described above.

In another aspect, the variant comprises or consists of substitutions at positions corresponding to positions 26, 76, and 208, such as those described above.

In another aspect, the variant comprises or consists of substitutions at positions corresponding to positions 26, 155, and 208, such as those described above.

In another aspect, the variant comprises or consists of substitutions at positions corresponding to positions 36, 37, and 155, such as those described above.

In another aspect, the variant comprises or consists of substitutions at positions corresponding to positions 36, 37, and 208, such as those described above.

In another aspect, the variant comprises or consists of substitutions at positions corresponding to positions 36, 155, and 208, such as those described above.

In another aspect, the variant comprises or consists of substitutions at positions corresponding to positions 37, 155, and 208, such as those described above.

In another aspect, the variant comprises or consists of substitutions at positions corresponding to positions 71, 74, and 75, such as those described above.

In another aspect, the variant comprises or consists of substitutions at positions corresponding to positions 71, 74, and 76, such as those described above.

In another aspect, the variant comprises or consists of substitutions at positions corresponding to positions 71, 74, and 155, such as those described above.

In another aspect, the variant comprises or consists of substitutions at positions corresponding to positions 71, 74, and 208, such as those described above.

In another aspect, the variant comprises or consists of substitutions at positions corresponding to positions 71, 75, and 76, such as those described above.

In another aspect, the variant comprises or consists of substitutions at positions corresponding to positions 71, 75, and 155, such as those described above.

In another aspect, the variant comprises or consists of substitutions at positions corresponding to positions 71, 75, and 208, such as those described above.

In another aspect, the variant comprises or consists of substitutions at positions corresponding to positions 71, 76, and 155, such as those described above.

In another aspect, the variant comprises or consists of substitutions at positions corresponding to positions 71, 76, and 208, such as those described above.

In another aspect, the variant comprises or consists of substitutions at positions corresponding to positions 71, 155, and 208, such as those described above.

In another aspect, the variant comprises or consists of substitutions at positions corresponding to positions 74, 75, and 76, such as those described above.

In another aspect, the variant comprises or consists of substitutions at positions corresponding to positions 74, 75, and 155, such as those described above.

In another aspect, the variant comprises or consists of substitutions at positions corresponding to positions 74, 75, and 208, such as those described above.

In another aspect, the variant comprises or consists of substitutions at positions corresponding to positions 74, 76, and 155, such as those described above.

In another aspect, the variant comprises or consists of substitutions at positions corresponding to positions 74, 76, and 208, such as those described above.

In another aspect, the variant comprises or consists of substitutions at positions corresponding to positions 74, 155, and 208, such as those described above.

In another aspect, the variant comprises or consists of substitutions at positions corresponding to positions 75, 76, and 155, such as those described above.

In another aspect, the variant comprises or consists of substitutions at positions corresponding to positions 75, 76, and 208, such as those described above.

In another aspect, the variant comprises or consists of substitutions at positions corresponding to positions 75, 155, and 208, such as those described above.

In another aspect, the variant comprises or consists of substitutions at positions corresponding to positions 76, 155, and 208, such as those described above.

In another aspect, the variant comprises or consists of substitutions at positions corresponding to positions 124, 155, and 208, such as those described above.

In another aspect, the variant comprises or consists of substitutions at positions corresponding to positions 133, 155, and 208, such as those described above.

In another aspect, the variant comprises or consists of substitutions at positions corresponding to positions 155, 167, and 208, such as those described above.

In another aspect, the variant comprises or consists of substitutions at positions corresponding to positions 24, 26, 71, and 74, such as those described above. In another aspect, the variant comprises or consists of substitutions at positions corresponding to positions 24, 26, 71, and 75, such as those described above.

In another aspect, the variant comprises or consists of substitutions at positions corresponding to positions 24, 26, 71, and 76, such as those described above.

In another aspect, the variant comprises or consists of substitutions at positions corresponding to positions 24, 26, 71, and 155, such as those described above.

In another aspect, the variant comprises or consists of substitutions at positions corresponding to positions 24, 26, 71, and 208, such as those described above.

In another aspect, the variant comprises or consists of substitutions at positions corresponding to positions 24, 71, 74, and 75, such as those described above. In another aspect, the variant comprises or consists of substitutions at positions corresponding to positions 24, 71, 74, and 76, such as those described above.

In another aspect, the variant comprises or consists of substitutions at positions corresponding to positions 24, 71, 74, and 155, such as those described above.

In another aspect, the variant comprises or consists of substitutions at positions corresponding to positions 24, 71, 74, and 208, such as those described above. In another aspect, the variant comprises or consists of substitutions at positions corresponding to positions 24, 74, 75, and 76, such as those described above.

In another aspect, the variant comprises or consists of substitutions at positions corresponding to positions 24, 74, 75, and 155, such as those described above.

In another aspect, the variant comprises or consists of substitutions at positions corresponding to positions 24, 74, 75, and 208, such as those described above.

In another aspect, the variant comprises or consists of substitutions at positions corresponding to positions 24, 74, 76, and 155, such as those described above.

In another aspect, the variant comprises or consists of substitutions at positions corresponding to positions 24, 74, 76, and 208, such as those described above. In another aspect, the variant comprises or consists of substitutions at positions corresponding to positions 24, 75, 76, and 155, such as those described above.

In another aspect, the variant comprises or consists of substitutions at positions corresponding to positions 24, 75, 76, and 208, such as those described above.

In another aspect, the variant comprises or consists of substitutions at positions corresponding to positions 24, 76, 155, and 208, such as those described above.

In another aspect, the variant comprises or consists of substitutions at positions corresponding to positions 26, 71, 74, and 75, such as those described above.

In another aspect, the variant comprises or consists of substitutions at positions corresponding to positions 26, 71, 74, and 76, such as those described above. In another aspect, the variant comprises or consists of substitutions at positions corresponding to positions 26, 71, 74, and 155, such as those described above.

In another aspect, the variant comprises or consists of substitutions at positions corresponding to positions 26, 71, 74, and 208, such as those described above.

In another aspect, the variant comprises or consists of substitutions at positions corresponding to positions 26, 74, 75, and 76, such as those described above.

In another aspect, the variant comprises or consists of substitutions at positions corresponding to positions 26, 74, 75, and 155, such as those described above.

In another aspect, the variant comprises or consists of substitutions at positions corresponding to positions 26, 74, 75, and 208, such as those described above. In another aspect, the variant comprises or consists of substitutions at positions corresponding to positions 26, 75, 76, and 155, such as those described above.

In another aspect, the variant comprises or consists of substitutions at positions corresponding to positions 26, 75, 76, and 208, such as those described above.

In another aspect, the variant comprises or consists of substitutions at positions corresponding to positions 26, 76, 155, and 208, such as those described above. In another aspect, the variant comprises or consists of substitutions at positions corresponding to positions 36, 37, 155, and 208, such as those described above.

In another aspect, the variant comprises or consists of substitutions at positions corresponding to positions 71, 74, 75, and 76, such as those described above.

In another aspect, the variant comprises or consists of substitutions at positions corresponding to positions 71, 74, 75, and 155, such as those described above.

In another aspect, the variant comprises or consists of substitutions at positions corresponding to positions 71, 74, 75, and 208, such as those described above.

In another aspect, the variant comprises or consists of substitutions at positions corresponding to positions 71, 75, 76, and 155, such as those described above. In another aspect, the variant comprises or consists of substitutions at positions corresponding to positions 71, 75, 76, and 208, such as those described above.

In another aspect, the variant comprises or consists of substitutions at positions corresponding to positions 71, 76, 155, and 208, such as those described above.

In another aspect, the variant comprises or consists of substitutions at positions corresponding to positions 74, 75, 76, and 155, such as those described above.

In another aspect, the variant comprises or consists of substitutions at positions corresponding to positions 74, 75, 76, and 208, such as those described above.

In another aspect, the variant comprises or consists of substitutions at positions corresponding to positions 74, 76, 155, and 208, such as those described above. In another aspect, the variant comprises or consists of substitutions at positions corresponding to positions 75, 76, 155, and 208, such as those described above.

In another aspect, the variant comprises or consists of substitutions at positions corresponding to positions 24, 26, 71, 74, and 75, such as those described above.

In another aspect, the variant comprises or consists of substitutions at positions corresponding to positions 24, 26, 71, 74, and 76, such as those described above.

In another aspect, the variant comprises or consists of substitutions at positions corresponding to positions 24, 26, 71, 74, and 155, such as those described above.

In another aspect, the variant comprises or consists of substitutions at positions corresponding to positions 24, 26, 71, 74, and 208, such as those described above. In another aspect, the variant comprises or consists of substitutions at positions corresponding to positions 24, 71, 74, 75, and 76, such as those described above.

In another aspect, the variant comprises or consists of substitutions at positions corresponding to positions 24, 71, 74, 75, and 155, such as those described above.

In another aspect, the variant comprises or consists of substitutions at positions corresponding to positions 24, 71, 74, 75, and 208, such as those described above. In another aspect, the variant comprises or consists of substitutions at positions corresponding to positions 24, 74, 75, 76, and 155, such as those described above.

In another aspect, the variant comprises or consists of substitutions at positions corresponding to positions 24, 74, 75, 76, and 208, such as those described above.

In another aspect, the variant comprises or consists of substitutions at positions corresponding to positions 24, 75, 76, 155, and 208, such as those described above.

In another aspect, the variant comprises or consists of substitutions at positions corresponding to positions 26, 71, 74, 75, and 76, such as those described above.

In another aspect, the variant comprises or consists of substitutions at positions corresponding to positions 26, 71, 74, 75, and 155, such as those described above. In another aspect, the variant comprises or consists of substitutions at positions corresponding to positions 26, 71, 74, 75, and 208, such as those described above.

In another aspect, the variant comprises or consists of substitutions at positions corresponding to positions 26, 74, 75, 76, and 155, such as those described above.

In another aspect, the variant comprises or consists of substitutions at positions corresponding to positions 26, 71, 74, 75, and 208, such as those described above.

In another aspect, the variant comprises or consists of substitutions at positions corresponding to positions 26, 74, 75, 76, and 155, such as those described above.

In another aspect, the variant comprises or consists of substitutions at positions corresponding to positions 26, 74, 75, 76, and 208, such as those described above. In another aspect, the variant comprises or consists of substitutions at positions corresponding to positions 26, 75, 76, 155, and 208, such as those described above.

In another aspect, the variant comprises or consists of substitutions at positions corresponding to positions 71, 74, 75, 76, and 155, such as those described above.

In another aspect, the variant comprises or consists of substitutions at positions corresponding to positions 71, 74, 75, 76, and 208, such as those described above.

In another aspect, the variant comprises or consists of substitutions at positions corresponding to positions 71, 75, 76, 155, and 208, such as those described above.

In another aspect, the variant comprises or consists of substitutions at positions corresponding to positions 74, 75, 76, 155, and 208, such as those described above. In another aspect, the variant comprises or consists of substitutions at positions corresponding to positions 24, 26, 71, 74, 75, and 76, such as those described above.

In another aspect, the variant comprises or consists of substitutions at positions corresponding to positions 24, 26, 71, 74, 75, and 155, such as those described above.

In another aspect, the variant comprises or consists of substitutions at positions corresponding to positions 24, 26, 71, 74, 75, and 208, such as those described above. In another aspect, the variant comprises or consists of substitutions at positions corresponding to positions 24, 71, 74, 75, 76, and 155, such as those described above.

In another aspect, the variant comprises or consists of substitutions at positions corresponding to positions 24, 71, 74, 75, 76, and 208, such as those described above.

In another aspect, the variant comprises or consists of substitutions at positions corresponding to positions 24, 74, 75, 76, 155, and 208, such as those described above.

In another aspect, the variant comprises or consists of substitutions at positions corresponding to positions 26, 71, 74, 75, 76, and 155, such as those described above.

In another aspect, the variant comprises or consists of substitutions at positions corresponding to positions 26, 71, 74, 75, 76, and 208, such as those described above. In another aspect, the variant comprises or consists of substitutions at positions corresponding to positions 26, 74, 75, 76, 155, and 208, such as those described above.

In another aspect, the variant comprises or consists of substitutions at positions corresponding to positions 71, 74, 75, 76, 155, and 208, such as those described above.

In another aspect, the variant comprises or consists of substitutions at positions corresponding to positions 24, 26, 71, 74, 75, 76, and 155, such as those described above.

In another aspect, the variant comprises or consists of substitutions at positions corresponding to positions 24, 26, 71, 74, 75, 76, and 208, such as those described above.

In another aspect, the variant comprises or consists of substitutions at positions corresponding to positions 24, 71, 74, 75, 76, 155, and 208, such as those described above. In another aspect, the variant comprises or consists of substitutions at positions corresponding to positions 26, 71, 74, 75, 76, 155, and 208, such as those described above.

In another aspect, the variant comprises or consists of substitutions at positions corresponding to positions 24, 26, 71, 74, 75, 76, 155, and 208, such as those described above.

In another aspect, the variant comprises or consists of one or more (e.g., several) substitutions selected from the group consisting of H24W, A26E, V74L, K75L, H76L, I155M, and V208L. In an embodiment, the variant has improved thermostability compared to the parent xylanase. In an embodiment, the parent xylanase is a *Bacillus* GH30 subfamily 8 xylanase, such as described below herein. In one embodiment, the parent xylanase is a *Bacillus subtilis* GH30 subfamily 8 xylanase, such as SEQ ID NO: 1 or SEQ ID NO: 4, preferably SEQ ID NO: 1. In one embodiment, the parent xylanase is a *Bacillus amyloliquefaciens* GH30 subfamily 8 xylanase, such as SEQ ID NO: 2 or SEQ ID NO: 6. In one embodiment, the parent xylanase is a *Bacillus licheniformis* GH30 subfamily 8 xylanase, such as SEQ ID NO: 3. In another aspect, the parent xylanase is a *Paenibacillus* GH30 subfamily 8 xylanase, such as described below herein. In one embodiment, the parent xylanase is a *Paenibacillus pabuli* GH30 subfamily 8 xylanase, such as SEQ ID NO: 5.

In another aspect, the variant comprises or consists of the substitutions H24W+A26E of the polypeptide of SEQ ID NO: 1.

In another aspect, the variant comprises or consists of the substitutions H24W+V74L of the polypeptide of SEQ ID NO: 1.

In another aspect, the variant comprises or consists of the substitutions H24W+K75L of the polypeptide of SEQ ID NO: 1.

In another aspect, the variant comprises or consists of the substitutions H24W+H76L of the polypeptide of SEQ ID NO: 1.

In another aspect, the variant comprises or consists of the substitutions H24W+I155M of the polypeptide of SEQ ID NO: 1.

In another aspect, the variant comprises or consists of the substitutions H24W+V208L of the polypeptide of SEQ ID NO: 1.

In another aspect, the variant comprises or consists of the substitutions A26E+V74L of the polypeptide of SEQ ID NO: 1.

In another aspect, the variant comprises or consists of the substitutions A26E+K75L of the polypeptide of SEQ ID NO: 1.

In another aspect, the variant comprises or consists of the substitutions A26E+H76L of the polypeptide of SEQ ID NO: 1.

In another aspect, the variant comprises or consists of the substitutions A26E+I155M of the polypeptide of SEQ ID NO: 1.

In another aspect, the variant comprises or consists of the substitutions A26E+V208L of the polypeptide of SEQ ID NO: 1.

In another aspect, the variant comprises or consists of the substitutions V74L+K75L of the polypeptide of SEQ ID NO: 1.

In another aspect, the variant comprises or consists of the substitutions V74L+H76L of the polypeptide of SEQ ID NO: 1.

In another aspect, the variant comprises or consists of the substitutions V74L+I155M of the polypeptide of SEQ ID NO: 1.

In another aspect, the variant comprises or consists of the substitutions V74L+V208L of the polypeptide of SEQ ID NO: 1.

In another aspect, the variant comprises or consists of the substitutions K75L+H76L of the polypeptide of SEQ ID NO: 1.

In another aspect, the variant comprises or consists of the substitutions K75L+I155M of the polypeptide of SEQ ID NO: 1.

In another aspect, the variant comprises or consists of the substitutions K75L+V208L of the polypeptide of SEQ ID NO: 1.

In another aspect, the variant comprises or consists of the substitutions H76L+I155M of the polypeptide of SEQ ID NO: 1.

In another aspect, the variant comprises or consists of the substitutions H76L+V208L of the polypeptide of SEQ ID NO: 1.

In another aspect, the variant comprises or consists of the substitutions I155M+V208L of the polypeptide of SEQ ID NO: 1.

The variants may further comprise one or more additional alterations at one or more (e.g., several) other positions.

In one embodiment, the invention relates to GH30 subfamily 8 xylanase variants having improved thermostability compared to the parent xylanase, comprising a substitution listed from the group consisting of:

| | | | | |
|---|---|---|---|---|
| 24, | 24 + 167, | 36 + 167, | 71 + 74, | 76 + 124, |
| 26, | 24 + 208, | 36 + 208, | 71 + 75, | 76 + 133, |
| 36, | 24 + 317, | 36 + 317, | 71 + 76, | 76 + 155, |
| 37, | 24 + 321, | 36 + 321, | 71 + 124, | 76 + 167, |
| 60, | 26 + 36, | 37 + 60, | 71 + 133, | 76 + 208, |
| 71, | 26 + 37, | 37 + 71, | 71 + 155, | 76 + 317, |
| 74, | 26 + 60, | 37 + 74, | 71 + 167, | 76 + 321, |
| 75, | 26 + 71, | 37 + 75, | 71 + 208, | 124 + 133, |
| 76, | 26 + 74, | 37 + 76, | 71 + 317, | 124 + 155, |
| 124, | 26 + 75, | 37 + 124, | 71 + 321, | 124 + 167, |
| 133, | 26 + 76, | 37 + 133, | 74 + 75, | 124 + 208, |
| 155, | 26 + 124, | 37 + 155, | 74 + 76, | 124 + 317, |
| 167, | 26 + 133, | 37 + 167, | 74 + 124, | 124 + 321, |
| 208, | 26 + 155, | 37 + 208, | 74 + 133, | 133 + 155, |
| 317, | 26 + 167, | 37 + 317, | 74 + 155, | 133 + 167, |
| 321, | 26 + 208, | 37 + 321, | 74 + 167, | 133 + 208, |
| 24 + 26, | 26 + 317, | 60 + 71, | 74 + 208, | 133 + 317, |
| 24 + 36, | 26 + 321, | 60 + 74, | 74 + 317, | 133 + 321, |
| 24 + 37, | 36 + 37, | 60 + 75, | 74 + 321, | 155 + 167, |
| 24 + 60, | 36 + 60, | 60 + 76, | 75 + 76, | 155 + 208, |
| 24 + 71, | 36 + 71, | 60 + 124, | 75 + 124, | 155 + 317, |
| 24 + 74, | 36 + 74, | 60 + 133, | 75 + 133, | 155 + 321, |
| 24 + 75, | 36 + 75, | 60 + 155, | 75 + 155, | 167 + 208, |
| 24 + 76, | 36 + 76, | 60 + 167, | 75 + 167, | 167 + 317, |
| 24 + 124, | 36 + 124, | 60 + 208, | 75 + 208, | 167 + 321, |
| 24 + 133, | 36 + 133, | 60 + 317, | 75 + 317, | 208 + 317, |
| 24 + 155, and | 36 + 155, 317 + 321. | 60 + 321, | 75 + 321, | 208 + 321, | wherein the positions correspond to the positions of SEQ ID NO: 1 and wherein the variant has xylanase activity and has at least 70% identity, preferably at least 80%, more preferably at least 85%, even more preferably at least 90%, or most preferably at least 95% identity to SEQ ID NO: 1. In an embodiment, the parent xylanase is a *Bacillus* GH30 subfamily 8 xylanase, such as described below herein. In one embodiment, the parent xylanase is a *Bacillus subtilis* GH30 subfamily 8 xylanase, such as SEQ ID NO: 1 or SEQ ID NO: 4, preferably SEQ ID NO: 1. In one embodiment, the parent xylanase is a *Bacillus amyloliquefaciens* GH30 subfamily 8 xylanase, such as SEQ ID NO: 2 or SEQ ID NO: 6. In one embodiment, the parent xylanase is a *Bacillus licheniformis* GH30 subfamily 8 xylanase, such as SEQ ID NO: 3. In another aspect, the parent xylanase is a *Paenibacillus* GH30 subfamily 8 xylanase, such as described below herein. In one embodiment, the parent xylanase is a *Paenibacillus pabuli* GH30 subfamily 8 xylanase, such as SEQ ID NO: 5.

In an embodiment, the substitution is selected from the group consisting of:

| | | | |
|---|---|---|---|
| A26E, | H76L, | K75L, | R60N, |
| E37L, | I155M, | K75N, | S317D, |
| E37T, | K71I, | K75T, | V208L, |
| F124Y, | K71L, | N167E, | V74I, |
| G321A, | K71T, | R36L, | V74L, |
| H24W, | K75E, | R36T, | Y133I, |
| H24W + A26E, | R36T + S317D, | K71I + K75T, | K75E + H76L, |
| H24W + R36L, | R36T + G321A, | K71I + H76L, | K75E + F124Y, |
| H24W + R36T, | E37L + R60N, | K71I + F124Y, | K75E + Y133I, |
| H24W + E37L, | E37L + K71I, | K71I + Y133I, | K75E + I155M, |
| H24W + E37T, | E37L + K71L, | K71I + I155M, | K75E + N167E, |
| H24W + R60N, | E37L + K71T, | K71I + N167E, | K75E + V208L, |
| H24W + K71I, | E37L + V74I, | K71I + V208L, | K75E + S317D, |
| H24W + K71L, | E37L + V74L, | K71I + S317D, | K75E + G321A, |
| H24W + K71T, | E37L + K75E, | K71I + G321A, | K75L + H76L, |
| H24W + V74I, | E37L + K75L, | K71L + V74I, | K75L + F124Y, |
| H24W + V74L, | E37L + K75N, | K71L + V74L, | K75L + Y133I, |
| H24W + K75E, | E37L + K75T, | K71L + K75E, | K75L + I155M, |
| H24W + K75L, | E37L + H76L, | K71L + K75L, | K75L + N167E, |
| H24W + K75N, | E37L + F124Y, | K71L + K75N, | K75L + V208L, |
| H24W + K75T, | E37L + Y133I, | K71L + K75T, | K75L + S317D, |
| H24W + H76L, | E37L + I155M, | K71L + H76L, | K75L + G321A, |
| H24W + F124Y, | E37L + N167E, | K71L + F124Y, | K75N + H76L, |
| H24W + Y133I, | E37L + V208L, | K71L + Y133I, | K75N + F124Y, |
| H24W + I155M, | E37L + S317D, | K71L + I155M, | K75N + Y133I, |
| H24W + N167E, | E37L + G321A, | K71L + N167E, | K75N + I155M, |
| H24W + V208L, | E37T + R60N, | K71L + V208L, | K75N + N167E, |
| H24W + S317D, | E37T + K71I, | K71L + S317D, | K75N + V208L, |
| H24W + G321A, | E37T + K71L, | K71L + G321A, | K75N + S317D, |
| R36L + E37L, | E37T + K71T, | K71T + V74I, | K75N + G321A, |
| R36L + E37T, | E37T + V74I, | K71T + V74L, | K75T + H76L, |
| R36L + R60N, | E37T + V74L, | K71T + K75E, | K75T + F124Y, |
| R36L + K71I, | E37T + K75E, | K71T + K75L, | K75T + Y133I, |
| R36L + K71L, | E37T + K75L, | K71T + K75N, | K75T + I155M, |
| R36L + K71T, | E37T + K75N, | K71T + K75T, | K75T + N167E, |
| R36L + V74I, | E37T + K75T, | K71T + H76L, | K75T + V208L, |
| R36L + V74L, | E37T + H76L, | K71T + F124Y, | K75T + S317D, |
| R36L + K75E, | E37T + F124Y, | K71T + Y133I, | K75T + G321A, |
| R36L + K75L, | E37T + Y133I, | K71T + I155M, | H76L + F124Y, |
| R36L + K75N, | E37T + I155M, | K71T + N167E, | H76L + Y133I, |
| R36L + K75T, | E37T + N167E, | K71T + V208L, | H76L + I155M, |
| R36L + H76L, | E37T + V208L, | K71T + S317D, | H76L + N167E, |
| R36L + F124Y, | E37T + S317D, | K71T + G321A, | H76L + V208L, |
| R36L + Y133I, | E37T + G321A, | V74I + K75E, | H76L + S317D, |
| R36L + I155M, | R60N + K71I, | V74I + K75L, | H76L + G321A, |
| R36L + N167E, | R60N + K71L, | V74I + K75N, | F124Y + Y133I, |
| R36L + V208L, | R60N + K71T, | V74I + K75T, | F124Y + I155M, |
| R36L + S317D, | R60N + V74I, | V74I + H76L, | F124Y + N167E, |
| R36L + G321A, | R60N + V74L, | V74I + F124Y, | F124Y + V208L, |
| R36T + E37L, | R60N + K75E, | V74I + Y133I, | F124Y + S317D, |
| R36T + E37T, | R60N + K75L, | V74I + I155M, | F124Y + G321A, |
| R36T + R60N, | R60N + K75N, | V74I + N167E, | Y133I + I155M, |
| R36T + K71I, | R60N + K75T, | V74I + V208L, | Y133I + N167E, |
| R36T + K71L, | R60N + H76L, | V74I + S317D, | Y133I + V208L, |
| R36T + K71T, | R60N + F124Y, | V74I + G321A, | Y133I + S317D, |
| R36T + V74I, | R60N + Y133I, | V74L + K75E, | Y133I + G321A, |
| R36T + V74L, | R60N + I155M, | V74L + K75L, | I155M + N167E, |
| R36T + K75E, | R60N + N167E, | V74L + K75N, | I155M + V208L, |
| R36T + K75L, | R60N + V208L, | V74L + K75T, | I155M + S317D, |
| R36T + K75N, | R60N + S317D, | V74L + H76L, | I155M + G321A, |
| R36T + K75T, | R60N + G321A, | V74L + F124Y, | N167E + V208L, |
| R36T + H76L, | K71I + V74I, | V74L + Y133I, | N167E + S317D, |
| R36T + F124Y, | K71I + V74L, | V74L + I155M, | N167E + G321A, |
| R36T + Y133I, | K71I + K75E, | V74L + N167E, | V208L + S317D, |
| R36T + I155M, | K71I + K75L, | V74L + V208L, | V208L + G321A, |
| R36T + N167E, | K71I + K75N, | V74L + S317D, | S317D + G321A, |
| R36T + V208L, | and | V74L + G321A. | |

The xylanase variant may further comprise one or more amino acid substitutions. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Asn/Gln, Gln/Glu, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In an embodiment, the variant has improved thermostability compared to the parent enzyme.

In one embodiment, the invention relates to a xylanase variant having xylanase activity, wherein:

(a) the xylanase variant comprises a substitution at one or more positions corresponding to positions 24, 26, 36, 37, 60, 71, 74, 75, 76, 124, 133, 155, 167, 208, 317, and 321 of SEQ ID NO: 1;

(b) the xylanase variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1; and (c) xylanase variant has improved thermostability compared to the parent xylanase.

In one embodiment, the invention relates to a xylanase variant having xylanase activity, wherein:

(a) the xylanase variant comprises a substitution at one or more positions corresponding to positions 24, 26, 60, 71, 74, 75, 76, 155, 208, 317, and 321 of SEQ ID NO: 1;

(b) the xylanase variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1; and (c) xylanase variant has improved thermostability compared to the parent xylanase.

In one embodiment, the invention relates to a xylanase variant having xylanase activity, wherein:

(a) the xylanase variant comprises one or more substitutions selected from the group consisting of H24W, A26E, R36L, R36T, E37T, R60N, K71T, K71I, V74L, V74I, K75N, K75L, H76L, I155M, N167E, V208L, S317D and G321A, wherein the positions correspond to the positions of SEQ ID NO: 1;

(b) the xylanase variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1; and (c) xylanase variant has improved thermostability compared to the parent xylanase.

In one embodiment, the invention relates to a xylanase variant having xylanase activity, wherein:

(a) the xylanase variant comprises one or more substitutions selected from the group consisting of H24W, A26E, R60N, K71T, K71I, V74L, V74I, K75N, K75L, H76L, I155M, V208L, S317D, G321A, R36T+I155M, R36L+I155M, I155M+N167E, R36T+V208L, R36L+V208L, N167E+V208L, E37T+V208L and R36T+E37T wherein the positions correspond to the positions of SEQ ID NO: 1;

(b) the xylanase variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1; and (c) xylanase variant has improved thermostability compared to the parent xylanase.

In one embodiment, the parent xylanase is SEQ ID NO: 1.

Parent Xylanases

In an embodiment, the parent xylanase is obtained or obtainable from the taxonomic order Bacillales, preferably the taxonimic family Bacillaceae, or more preferably from the genus *Bacillus subtilis, Bacillus amyloliquefaciens, Bacillus licheniformis* or *Paenibacillus pabuli*. In one embodiment, the parent xylanase is obtained or obtainable from the taxonomic order Bacillales, preferably the taxonimic family Bacillaceae and has at least 70% identity, preferably at least 80%, more preferably at least 85%, even more preferably at least 90%, or most preferably at least 95% identity to SEQ ID NO: 1.

In an embodiment, the parent xylanase is a GH30 subfamily 8 xylanase. In an embodiment, the parent xylanase is a *Bacillus* GH30 subfamily 8 xylanase, such as described below herein. In one embodiment, the parent xylanase is a *Bacillus subtilis* GH30 subfamily 8 xylanase, such as SEQ ID NO: 1 or SEQ ID NO: 4, preferably SEQ ID NO: 1. In one embodiment, the parent xylanase is a *Bacillus amyloliquefaciens* GH30 subfamily 8 xylanase, such as SEQ ID NO: 2 or SEQ ID NO: 6. In one embodiment, the parent xylanase is a *Bacillus licheniformis* GH30 subfamily 8 xylanase, such as SEQ ID NO: 3. In another aspect, the parent xylanase is a *Paenibacillus* GH30 subfamily 8 xylanase, such as described below herein. In one embodiment, the parent xylanase is a *Paenibacillus pabuli* GH30 subfamily 8 xylanase, such as SEQ ID NO: 5.

The parent xylanase may be (a) a polypeptide having at least 60% sequence identity to SEQ ID NO: 1, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 1. In another aspect, the parent comprises or consists of the amino acid sequence of SEQ ID NO: 1. In another aspect, the parent is a fragment of SEQ ID NO: 1 which has xylanase activity.

The parent xylanase may be (a) a polypeptide having at least 60% sequence identity to SEQ ID NO: 2, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 2. In another aspect, the parent comprises or consists of the amino acid sequence of SEQ ID NO: 2. In another aspect, the parent is a fragment of SEQ ID NO: 2 which has xylanase activity.

The parent xylanase may be (a) a polypeptide having at least 60% sequence identity to SEQ ID NO: 3, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 3. In another aspect, the parent comprises or consists of the amino acid sequence of SEQ ID NO: 3. In another aspect, the parent is a fragment of SEQ ID NO: 3 which has xylanase activity.

The parent xylanase may be (a) a polypeptide having at least 60% sequence identity to SEQ ID NO: 4, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 4. In another aspect, the parent comprises or consists of the amino acid sequence of SEQ ID NO: 4. In another aspect, the parent is a fragment of SEQ ID NO: 4 which has xylanase activity.

The parent xylanase may be (a) a polypeptide having at least 60% sequence identity to SEQ ID NO: 5, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 5. In another aspect, the parent comprises or consists of the amino acid sequence of SEQ ID NO: 5. In another aspect, the parent is a fragment of SEQ ID NO: 5 which has xylanase activity.

The parent xylanase may be (a) a polypeptide having at least 60% sequence identity to SEQ ID NO: 6, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from SEQ ID NO: 6. In another aspect, the parent comprises or consists of the amino acid sequence of SEQ ID NO: 6. In another aspect, the parent is a fragment of SEQ ID NO: 6 which has xylanase activity.

Other parent xylanases may be one of the following GENESEQP accession numbers: BCM03690, BBY25441, BBD43833, AZG87760, BBW75090, BCM03682, BBW96675, BCM03671, ADJ35022, BBW83525, BCM03685, BBW88031, BCM03707, AZH70238, AZG87766, BBX36748, BCM03686, AZQ23477, BCM03677, BCM03691, BCM03681, BCM03676, BCM03688, AZG68558, ADJ35028, BCM03687, BBG80964, AZX66647, AZH70244, BCM03689, AZM95903, BBW79314, BBX47049, BCM03683, BCM03679, BBW95840, BBX52401, BBW92246, BBX42063 and AZG68552.

Other parent xylanases may be one of the following UniProt accession numbers: A0A016QIT0, A0A024BEN2, A0A059N8P2, A0A060J1Q4, A0A060J3N3, A0A060MDP8, A0A063XEB2, A0A063Z3F5, A0A066ZQH2, A0A068QG80, A0A069DJA1, A0A074QA16, A0A076GH62, A0A076X095, A0A080UGI0, A0A081DRH7, A0A081L9P3, A0A085CCQ4, A0A086DRT4, A0A086SGC4, A0A086WWT9, A0A089J0T9, A0A089L7Q4, A0A089LS30, A0A089MA96, A0A089MMY5, A0A090ZY18, A0A093UG96, A0A097RET6, A0A097RT57, A0A0A0TJX0, A0A0A0TS05, A0A0A1STB1, A0A0A7GLZ8, A0A0A8C3V5, A0A0B0QGI0, A0A0B4S841, A0A0C2TMZ1, A0A0C5CYD2, A0A0D7XHL0, A0A0D7XPV8, A0A0D8JJW7, A0A0E1LNG3, A0A0E1P2T5, A0A0F5MCQ0, A0A0F5YUV2, A0A0G2M1V3, A0A0G2Z099, A0A0G3VDP8, A0A0H1RW51, A0A0H3DZC9, A0A0J1HNE5, A0A0J118S6, A0A0J5XBB3, A0A0J6E3H1, A0A0J6ENY2, A0A0J6MZ81, A0A0J6PTT5, A0A0K0HYL4, A0A0K6JZ62, A0A0K6L1E5, A0A0K6L5C0, A0A0K6LRC5, A0A0K6MBZ9, A0A0K9E179, A0A0K9G2M8, A0A0L6C9N3, A0A0L7MT05, A0A0L7SGL4, A0A0M0HBT0, A0A0M2E136, A0A0M2S6E2, A0A0M9X369, A0A0P0TKN9, A0A0P7GC51, A0A0Q3W7T1, A0A0Q4R817, A0A0Q7SDS0, A0A0R3K873, A0A0T6LD54, A0A0U3M226, A0A0U5Q000, A0A0V8QN06, A0A0V8QPQ0, A0A0V8RCK0, A0A0W1Q0Y8, A0A0W7X148, A0A0W8K830, A0A0X1TCR2, A0A0X8C7K8, A0A0X8DHN5, A0A0X8KDH2, A0A0X9LBN0, A0A101YC92, A0A101YL97, A0A117SZP6, A0A124JQM2, A0A125UIF6, A0A127DQZ4, A0A132BP80, A0A132TGU4, A0A132TSQ5, A0A136AEB9, A0A142F586, A0A150L2Y6, A0A160EHD0, A0A164XMN2, A0A172HNW1, A0A172XIR5, A0A199N163, A0A199WHT5, A0A1A0CC44, A0A1A0G7Q3, A0A1A5VV23, A0A1A5YLD9, A0A1A7LKF3, A0A1B2AW76, A0A1C3SIT4, A0A1C4AHG6, A0A1D9PK78, A0A1E4Y0F1, A0A1G9MAD1, A0A1J0BBP6, A0A1J0C717, A0A1J5WRC5, A0A1J6F1D5, A0A1K1TBA7, A0A1L3PT45, A0A1L3QY16, A0A1L3SH52, A0A1L4DM20, A0A1L5LNU4, A0A1L6CEM3, A0A1L6ZLN8, A0A1L6ZTD9, A0A1M7SMM4, A0A1N6S500, A0A1N7B930, A0A1N7E7E0, A0A1R1E8G3, A0A1R1ESJ7, A0A1R1FQ77, A0A1R1GBK8, A0A1R1GT02, A0A1R1HH77, A0A1S2F2R2, A0A1U3ULV5, A7Z5A1, A8FDV2, B3KF38, D1MEP8, D3EH02, D4FXC2, E0RDU2, E1ACF9, E1UV03, E3E322, E8VJ45, F4E4B0, F4EKU6, G0IKW9, G4EVQ6, G4HGL4, G4P7F1, G7W2J1, H0FNN1, H1ACZ7, H2AJ54, H3K352, H6CPJ0, H6WCZ0, H8XMR3, I4XB64, J0X3V6, J7JVZ4, K2HJT3, K2P3H7, L0BLZ3, L0CY72, L8AKB2, M1KJT1, M1U2J5, M1XAU4, M2U9N8, N0DFI8, Q45070, Q6YK37, Q70K02, R9TYN3, S6FS40, S6FXS9, U1T362, U1ZC44, U2TM90, U4PL99, U5X5B8, V5MRU9, V7Q6M1, V9REY3, W4AZH7, W4BX14, W4C6X9, W4D801, W4DEL3, W81LG7 and W9TFT6.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having xylanase activity. In one embodiment, the polypeptide is from a bacterium of the class Bacilli, such as from the order Bacillales, or from the family Paenibacillaceae, or from the genus *Paenibacillus* or from the species *Paenibacillus* sp-19179 or *Paenibacillus panacisoli.*

In another embodiment, the polypeptide is from a bacterium of the class Clostridia, such as from the order Clostridiales, or from the family Clostridiaceae, or from the genus *Clostridium* or from the species *Clostridium saccharobutylicum.*

In another embodiment, the polypeptide is from a bacterium of the class Clostridia, such as from the order Clostridiales, or from the family Ruminococcaceae, or from the genus *Ruminococcus*, or from the species *Ruminococcus* sp. CAG:330.

In another embodiment, the polypeptide is from a bacterium of the class Gammaproteobacteria, such as from the order Alteromonadales, or from the family Pseudoalteromonadaceae, or from the genus *Pseudoalteromonas* or from the species *Pseudoalteromonas tetraodonis.*

In another embodiment, the polypeptide is from a bacterium of the class Gammaproteobacteria, such as from the order Enterobacteriales, or from the family Enterobacteriaceae, or from the genus *Pectobacterium* or from the species *Pectobacterium carotovorum.*

In another embodiment, the polypeptide is from a bacterium of the class Actinobacteria, such as from the order Streptomycetales, or from the family Streptomycetaceae, or from the genus *Streptomyces* or from the species *Streptomyces* sp-62627.

In another embodiment, the polypeptide is from a bacterium of the class Gammaproteobacteria, such as from the order Vibrionales, or from the family Vibrionaceae, or from the genus *Vibrio* or from the species *Vibrio rhizosphaerae.*

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* xylanase.

In another aspect, the parent is a *Streptococcus equisimilis, Streptococcus pyogenes, Streptococcus uberis,* or *Streptococcus equi* subsp. *Zooepidemicus* xylanase.

In another aspect, the parent is a *Bacillus subtilis* xylanase, e.g., the xylanase having the amino acid sequence of SEQ ID NO: 1.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having xylanase activity, comprising: (a) introducing into a parent xylanase a substitution at one or more (e.g., several) positions corresponding to positions 24, 26, 36, 37, 60, 71, 74, 75, 76, 124, 133, 155, 167, 208, 317, and 321 of SEQ ID NO: 1, wherein the variant has xylanase activity; and (b) recovering the variant. In an embodiment, the variant has at least 70% identity, preferably at least 80%, more preferably at least 85%, even more preferably at least 90%, or most preferably at least 95% identity to SEQ ID NO: 1. In an embodiment, the parent xylanase has at least 70% identity, preferably at least 80%, more preferably at least 85%, even more preferably at least 90%, or most preferably at least 95% identity to SEQ ID NO: 1. In one embodiment, the substitution is selected from the group consisting of H24W, A26E, R36L, R36T, E37T, R60N, K71T, K71I, V74L, V74I, K75N, K75L, H76L, I155M, N167E, V208L, S317D and G321A. The invention further relates to a xylanase variant produced by the method herein described.

In one embodiment, the invention relates to a method for obtaining a variant having xylanase activity and having improved thermostability compared to a parent xylanase, wherein the parent xylanase is a GH30 subfamily 8 xylanase, comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 wherein the positions correspond to the positions of SEQ ID NO: 1, wherein the variant has at least 70% identity, preferably at least 80%, more preferably at least 85%, even more preferably at least 90%, or most preferably at least 95% identity to SEQ ID NO: 1; and (b) recovering the variant. In an embodiment, the parent xylanase has at least 70% identity, preferably at least 80%, more preferably at least 85%, even more preferably at least 90%, or most preferably at least 95% identity to SEQ ID NO: 1. In one embodiment, the substitution is selected from the group consisting of H24W, A26E, R36L, R36T, E37T, R60N, K71T, K71I, V74L, V74I, K75N, K75L, H76L, I155M, N167E, V208L, S317D and G321A. The invention further relates to a xylanase variant produced by the method herein described.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 1 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 1, wherein the variant has at least 70% identity, preferably at least 80%, more preferably at least 85%, even more preferably at least 90%, or most preferably at least 95%, to SEQ ID NO: 1; and (b) recovering the variant. In one embodiment, the substitution is selected from the group consisting of H24W, A26E, R36L, R36T, E37T, R60N, K71T, K71I, V74L, V74I, K75N, K75L, H76L, I155M, N167E, V208L, S317D and G321A. The invention further relates to a xylanase variant produced by the method herein described.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 2 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 2, wherein the variant has at least 70% identity, preferably at least 80%, more preferably at least 85%, even more preferably at least 90%, or most preferably at least 95% identity to SEQ ID NO: 2; and (b) recovering the variant.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 3 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 3, wherein the variant has at least 70% identity, preferably at least 80%, more preferably at least 85%, even more preferably at least 90%, or most preferably at least 95% identity to SEQ ID NO: 3; and (b) recovering the variant.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 4 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 4, wherein the variant has at least 70% identity, preferably at least 80%, more preferably at least 85%, even more preferably at least 90%, or most preferably at least 95% identity to SEQ ID NO: 4; and (b) recovering the variant.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 5 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 5, wherein the variant has at least 70% identity, preferably at least 80%, more preferably at least 85%, even more preferably at least 90%, or most preferably at least 95% identity to SEQ ID NO: 5; and (b) recovering the variant.

In one embodiment, the invention relates to a method for obtaining a variant having xylanase activity and having improved thermostability compared to a parent xylanase, wherein the parent xylanase has at least 70% identity, preferably at least 80%, more preferably at least 85%, even more preferably at least 90%, or most preferably at least 95% identity to SEQ ID NO: 6 comprising: (a) introducing into the parent xylanase a substitution at one or more (e.g., several) positions selected from the group consisting of 24, 26, 36, 37, 60, 71, 74, 75, 76, 124, 133, 155, 167, 208, 317, and 321 of SEQ ID NO: 6, wherein the variant has at least 70% identity, preferably at least 80%, more preferably at least 85%, even more preferably at least 90%, or most preferably at least 95% identity to SEQ ID NO: 6; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector may contain one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector may contain an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense*,

*Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the xylanase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the composition comprises the polypeptide of the invention and one or more formulating agents, as described below.

The compositions may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, glucan 1,4-α-glucosidase, glucan 1,4-alpha-maltohydrolase, glucan 1,4-α-glucosidase, glucan 1,4-alpha-maltohydrolase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The compositions may further comprise one or more microbes. In an embodiment, the microbe is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococcus acidilactici*, *Pediococcus* sp., *Propionibacterium thoenii*, *Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

In an embodiment, the composition comprises plant based material from the sub-family Panicoideae as disclosed herein, preferably maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof.

Formulation

The enzyme of the invention may be formulated as a liquid or a solid. For a liquid formulation, the formulating agent may comprise a polyol (such as, e.g., glycerol, ethylene glycol or propylene glycol), a salt (such as, e.g., sodium chloride, sodium benzoate, potassium sorbate) or a sugar or sugar derivative (such as, e.g., dextrin, glucose, sucrose, and sorbitol). Thus, in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g., as disclosed in WO 00/70034). The formulating agent may comprise a salt (organic or inorganic zinc, sodium, potassium or calcium salts such as, e.g., calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol).

In one embodiment, the composition is a solid composition, such as a spray dried composition, comprising the xylanase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the xylanase of the invention optionally combined with one or more additional enzymes. The granule is composed of a core, and optionally one or more coatings (outer layers) surrounding the core.

Typically, the granule/particle size, measured as equivalent spherical diameter (volume based average particle size), of the granule is 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. U.S. Pat. Nos. 4,016,040 and 4,713,245 also relate to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as, e.g., sucrose, dextrin, glucose, lactose, sorbitol), sugar or sugar derivative (such as, e.g., sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO 97/05245, WO 98/54980, WO 98/55599, WO 00/70034, WO 2006/034710, WO 2008/017661, WO 2008/017659, WO 00/020569, WO 01/04279, WO 97/05245, WO 00/01793, WO 2003/059086, WO 2003/059087, WO 2007/031483, WO 2007/031485, WO 2007/044968, WO 2013/192043, WO 2014/014647 and WO 2015/197719 or polymer coating such as described in WO 01/00042.

Specific examples of suitable salts are NaCl (CH20° C.=76%), Na$_2$CO$_3$ (CH20° C.=92%), NaNO$_3$ (CH20° C.=73%), Na$_2$HPO$_4$ (CH20° C.=95%), Na$_3$PO$_4$ (CH25° C.=92%), NH$_4$Cl (CH20° C.=79.5%), (NH$_4$)$_2$HPO$_4$ (CH20° C.=93.0%), NH$_4$H$_2$PO$_4$ (CH20° C.=93.1%), (NH$_4$)$_2$SO$_4$ (CH20° C.=81.1%), KCl (CH20° C.=85%), K$_2$HPO$_4$ (CH20° C.=92%), KH$_2$PO$_4$ (CH20° C.=96.5%), KNO$_3$ (CH20° C.=93.5%), Na$_2$SO$_4$ (CH20° C.=93%), K$_2$SO$_4$ (CH20° C.=98%), KHSO$_4$ (CH20° C.=86%), MgSO$_4$ (CH20° C.=90%), ZnSO$_4$ (CH20° C.=90%) and sodium citrate (CH25° C.=86%). Other examples include NaH$_2$PO$_4$, (NH$_4$)H$_2$PO$_4$, CuSO$_4$, Mg(NO$_3$)$_2$, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e., a crystalline salt hydrate with bound water(s) of crystallization, such as described in WO 99/32595. Specific examples include anhydrous sodium sulfate (Na$_2$SO$_4$), anhydrous magnesium sulfate (MgSO$_4$), magnesium sulfate heptahydrate (MgSO$_4$.7H$_2$O), zinc sulfate heptahydrate (ZnSO$_4$.7H$_2$O), sodium phosphate dibasic heptahydrate (Na$_2$HPO$_4$.7H$_2$O), magnesium nitrate hexahydrate (Mg(NO$_3$)$_2$(6H$_2$O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the xylanase of the invention, one or more salt coatings and one or more wax coatings. Examples of enzyme granules with multiple coatings are shown in WO 93/07263, WO 97/23606 and WO 2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:

(a) a core comprising an xylanase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed compositions and animal feed additives comprising one or more xylanases of the invention. In an embodiment, the animal feed or animal feed additive comprises a formulating agent and one or more xylanases of the invention. In a further embodiment, the formulating agent comprises one or more of the following compounds: glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose.

Thus the invention further relates to an animal feed additive comprising one or more vitamins and a xylanase variant of the invention. The invention also relates to an animal feed additive comprising one or more minerals and a xylanase variant of the invention. The invention also relates to an animal feed additive comprising one or more amino acids and a xylanase variant of the invention.

In an embodiment, the amount of enzyme in the animal feed additive is between 0.001% and 10% by weight of the composition.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more xylanase variants of the invention. The invention also relates to an animal feed comprising the granule as described herein and plant based material. The invention also relates to an animal feed comprising the animal feed additive as described herein and plant based material. In one embodiment, the plant based material is from the sub-family Panicoideae.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore, such fish diets usually have a crude fat content of 200-310 g/kg.

An animal feed composition according to the invention has a crude protein content of 50-800 g/kg, and furthermore comprises at least one xylanase as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% *sorghum*; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g., beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can, e.g., be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) xylanase/enzyme preparation may also be added before or during the feed ingredient step. Typically, a liquid xylanase/enzyme preparation comprises the xylanase of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the xylanase can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10;—all these ranges being in mg xylanase protein per kg feed (ppm).

For determining mg xylanase protein per kg feed, the xylanase is purified from the feed composition, and the specific activity of the purified xylanase is determined using a relevant assay (see under xylanase activity). The xylanase activity of the feed composition as such is also determined using the same assay, and on the basis of these two determinations, the dosage in mg xylanase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg xylanase protein in feed additives. Of course, if a sample is available of the xylanase used for preparing the feed additive or the feed, the specific activity is determined from this sample (no need to purify the xylanase from the feed composition or the additive).

Plant Based Material from the Sub-Family Panicoideae

In one embodiment, the plant based material from the sub-family Panicoideae is from the tribe Andropogoneae such as the rank *Andropogon* or *Andropterum* or *Apluda* or *Apocopis* or *Arthraxon* or *Bothriochloa* or *Capillipedium* or *Chionachne* or *Chrysopogon* or *Coelorachis* or *Coix* or *Cymbopogon* or *Dichanthium* or *Diheteropogon* or *Dimeria* or *Elionurus* or *Eremochloa* or *Euclasta* or *Eulalia* or *Germainia* or *Hemarthria* or *Heteropholis* or *Heteropogon* or *Hyparrhenia* or *Hyperthelia* or *Imperata* or *Ischaemum* or *Iseilema* or *Kerriochloa* or *Microstegium* or *Miscanthidium* or *Miscanthus* or *Mnesithea* or *Ophiuros* or *Oxyrhachis* or *Phacelurus* or *Pholiurus* or *Pogonatherum* or *Polytoca* or *Polytrias* or *Pseudopogonatherum* or *Pseudosorghum* or *Rhytachne* or *Rottboellia* or *Saccharum* (e.g., sugar cane) or *Sarga* or *Schizachyrium* or *Sehima* or *Sorghastrum* or *Sorghum* or *Spodiopogon* or *Thaumastochloa* or *Thelepogon* or *Themeda* or *Trachypogon* or *Triarrhena* or *Tripsacum* or *Urelytrum* or *Vetiveria* or *Vossia* or *Xerochloa* or *Zea*.

In a preferred embodiment, the plant based material from the sub-family Panicoideae is from the rank *Zea*, such as the species *Zea diploperennis*, *Zea luxurians*, *Zea mays*, *Zea nicaraguensis* or *Zea perennis*.

In a preferred embodiment, the plant based material from the sub-family Panicoideae is from the rank *Sorghum*, such as the species *Sorghum amplum*, *Sorghum angustum*, *Sorghum arundinaceum*, *Sorghum australiense*, *Sorghum bicolor*, *Sorghum brachypodum*, *Sorghum bulbosum*, *Sorghum ecarinatum*, *Sorghum exstans*, *Sorghum grande*, *Sorghum halepense*, *Sorghum hybrid cultivar*, *Sorghum interjectum*, *Sorghum intrans*, *Sorghum laxiflorum*, *Sorghum leiocladum*, *Sorghum macrospermum*, *Sorghum matarankense*, *Sorghum nitidum*, *Sorghum plumosum*, *Sorghum propinquum*, *Sorghum purpureosericeum*, *Sorghum stipoideum*, *Sorghum sudanense*, *Sorghum timorense*, *Sorghum versicolor*, *Sorghum* sp. 'Silk' or *Sorghum* sp. as defined in WO 2007/002267.

In another embodiment, the plant based material from the sub-family Panicoideae is from the tribe Paniceae such as the rank *Acritochaete*, *Acroceras*, *Alexfloydia*, *Alloteropsis*, *Amphicarpum*, *Ancistrachne*, *Anthephora*, *Brachiaria* (e.g., signal grass), *Calyptochloa*, *Cenchrus*, *Chaetium*, *Chaetopoa*, *Chamaeraphis*, *Chlorocalymma*, *Cleistochloa*, *Cyphochlaena*, *Cyrtococcum*, *Dichanthelium*, *Digitaria*, *Dissochondrus*, *Echinochloa*, *Entolasia*, *Eriochloa*, *Homopholis*, *Hygrochloa*, *Hylebates*, *Ixophorus*, *Lasiacis*, *Leucophrys*, *Louisiella*, *Megaloprotachne*, *Megathyrsus*, *Melinis*, *Microcalamus*, *Moorochloa*, *Neurachne*, *Odontelytrum*, *Oplismenus*, *Ottochloa*, *Panicum*, *Paractaenum*, *Paraneurachne*, *Paratheria*, *Parodiophyllochloa*, *Paspalidium*, *Pennisetum*, *Plagiosetum*, *Poecilostachys*, *Pseudechinolaena*, *Pseudochaetochloa*, *Pseudoraphis*, *Rupichloa*, *Sacciolepis*, *Scutachne*, *Setaria*, *Setariopsis*, *Snowdenia*, *Spinifex*, *Stenotaphrum*, *Stereochlaena*, *Thrasya*, *Thuarea*, *Thyridolepis*, *Tricholaena*, unclassified Paniceae, *Uranthoecium*, *Urochloa* (e.g., signal grass), *Walwhalleya*, *Whiteochloa*, *Yakirra*, *Yvesia*, *Zuloagaea* or *Zygochloa*.

In a preferred embodiment, the plant based material from the sub-family Panicoideae is from the rank *Panicum*, such as the species *Panicum adenophorum*, *Panicum* aff. *aquaticum* JKT-2012, *Panicum amarum*, *Panicum antidotale*, *Panicum aquaticum*, *Panicum arctum*, *Panicum arundinariae*, *Panicum atrosanguineum*, *Panicum auricomum*, *Panicum auritum*, *Panicum bartlettii*, *Panicum Panicum bisulcatum*, *Panicum boliviense*, *Panicum brazzavillense*, *Panicum brevifolium*, *Panicum caaguazuense*, *Panicum campestre*, *Panicum capillare*, *Panicum cayennense*, *Panicum cayoense*, *Panicum cervicatum*, *Panicum chloroleucum*, *Panicum claytonii*, *Panicum coloratum*, *Panicum cyanescens*, *Panicum decompositum*, *Panicum deustum*, *Panicum dichotomiflorum*, *Panicum dinklagei*, *Panicum distichophyllum*, *Panicum dregeanum*, *Panicum elephantipes*, *Panicum fauriei*, *Panicum flexile*, *Panicum fluviicola*, *Panicum Panicum gracilicaule*, *Panicum granuliferum*, *Panicum guatemalense*, *Panicum hallii*, *Panicum heterostachyum*, *Panicum hirticaule*, *Panicum hirtum*, *Panicum hylaeicum*, *Panicum incumbens*, *Panicum infestum*, *Panicum italicum*, *Panicum laetum*, *Panicum laevinode*, *Panicum lanipes*, *Panicum larcomianum*, *Panicum longipedicellatum*, *Panicum machrisianum*, *Panicum malacotrichum*, *Panicum mar-*

*garitiferum, Panicum micranthum, Panicum miliaceum, Panicum milioides, Panicum millegrana, Panicum mystasipum, Panicum natalense, Panicum nephelophilum, Panicum nervosum, Panicum notatum, Panicum olyroides, Panicum paludosum, Panicum pansum, Panicum pantrichum, Panicum parvifolium, Panicum parviglume, Panicum pedersenii, Panicum penicillatum, Panicum petersonii, Panicum phragmitoides, Panicum piauiense, Panicum pilosum, Panicum pleianthum, Panicum polycomum, Panicum polygonatum, Panicum pseudisachne, Panicum pygmaeum, Panicum pyrularium, Panicum queenslandicum, Panicum racemosum, Panicum repens, Panicum rhizogonum, Panicum rigidulum, Panicum rivale, Panicum rude, Panicum rudgei, Panicum schinzii, Panicum schwackeanum, Panicum sellowii, Panicum seminudum, Panicum stapfianum, Panicum stenodes, Panicum stramineum, Panicum subalbidum, Panicum subtiramulosum, Panicum sumatrense, Panicum tenellum, Panicum tenuifolium, Panicum trichanthum, Panicum trichidiachne, Panicum trichoides, Panicum tricholaenoides, Panicum tuerckheimii, Panicum turgidum, Panicum urvilleanum, Panicum validum, Panicum venezuelae, Panicum verrucosum, Panicum virgatum, Panicum wettsteinii, Panicum sp., Panicum sp. Christin 16-200, Panicum sp. ELS-2011, Panicum sp. EM389 or Panicum sp.* Forest 761.

In a further embodiment, the plant based material from the sub-family Panicoideae is maize (*Zea*), corn (*Zea*), sorghum (*Sorghum*), switchgrass (*Panicum virgatum*), millet (*Panicum miliaceum*), pearl millet (*Cenchrus violaceus* also called *Pennisetum glaucum*), foxtail millet (*Setaria italica* also called *Panicum italicum*) or in a processed form such as milled corn, milled maize, defatted maize, defatted destarched maize, milled *sorghum*, milled switchgrass, milled millet, milled foxtail millet, milled pearl millet, or any combination thereof.

In an embodiment, the plant based material from the sub-family Panicoideae is from the seed of the plant. In a preferred embodiment, the plant based material from the sub-family Panicoideae is from the seed of maize (*Zea*), corn (*Zea*), sorghum (*Sorghum*), switchgrass (*Panicum virgatum*), millet (*Panicum miliaceum*), pearl millet (*Cenchrus violaceus* also called *Pennisetum glaucum*), foxtail millet (*Setaria italica* also called *Panicum italicum*) or wherein the seed has been processed such as milled corn, milled maize, defatted maize, defatted destarched maize, milled *sorghum*, milled switchgrass, milled millet, milled foxtail millet, milled pearl millet, or any combination thereof.

In another embodiment, the compositions described herein optionally include one or more enzymes. Enzymes can be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al., 2014, "The carbohydrate-active enzymes database (CAZy) in 2013", *Nucl. Acids Res.* 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, 2000, The ENZYME database, *Nucleic Acids Res.* 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al., 2014, "The carbohydrate-active enzymes database (CAZy) in 2013", *Nucl. Acids Res.* 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), glucan 1,4-α-glucosidase (glucoamylase) (EC 3.2.1.3), glucan 1,4-alpha-maltohydrolase (maltogenic alpha-amylase) (EC 3.2.1.133), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectinesterase (EC 3.1.1.11), xylanase (EC 3.2.1.8, EC 3.2.1.136), beta-xylosidase (EC 3.2.1.37), or any combination thereof.

In a particular embodiment the composition of the invention comprises a galactanase (EC 3.2.1.89) and a beta-galactosidase (EC 3.2.1.23).

In a particular embodiment the composition of the invention comprises an alpha-galactosidase (EC 3.2.1.22).

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), Ave-Mix® Phytase (Aveve Biochem), Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), Ave-Mix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococcus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day. In one embodiment, the amount of probiotics is 0.001% to 10% by weight of the composition.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

In one embodiment, the amount of prebiotics is 0.001% to 10% by weight of the composition. Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and *curcuma* extract.

In one embodiment, the amount of phytogeneics is 0.001% to 10% by weight of the composition. Examples of commercial products are Crina® (DSM Nutritional Products); Cinergy™, Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

In one embodiment, the amount of organic acid is 0.001% to 10% by weight of the composition. Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of microingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan. In one embodiment, the amount of amino acid is 0.001% to 10% by weight of the composition.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

In one embodiment, the amount of vitamins is 0.001% to 10% by weight of the composition. In one embodiment, the amount of minerals is 0.001% to 10% by weight of the composition.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, antifungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in nmegative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, *sorghum*, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Uses

The present invention is also directed to methods for using the xylanase variants, or compositions thereof, for, e.g., animal feed, processes for producing a fermentation product and in baking. The present invention is also directed to processes for using the xylanase variants, or compositions thereof, such as, e.g., those described below.

Use in Animal Feed

The present invention is also directed to methods for using the xylanase variants in animal feed.

The term animal includes all animals. Examples of animals are non-ruminants, and ruminants. Ruminant animals include, for example, animals such as sheep, goats, and cattle, e.g., beef cattle, cows, and young calves. In a particular embodiment, the animal is a non-ruminant animal. Non-ruminant animals include mono-gastric animals, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

In the use according to the invention the xylanase variants can be fed to the animal before, after, or simultaneously with the diet. The latter is preferred.

In a particular embodiment, the form in which the xylanase variant is added to the feed, or animal feed additive, is well-defined. Well-defined means that the xylanase and/or arabinofuranosidase preparation is at least 50% pure as determined by Size-exclusion chromatography (see Example 12 of WO 01/58275). In other particular embodiments, the xylanase and/or arabinofuranosidase preparation is at least 60, 70, 80, 85, 88, 90, 92, 94, or at least 95% pure as determined by this method.

A well-defined xylanase preparation is advantageous. For instance, it is much easier to dose correctly to the feed a xylanase that is essentially free from interfering or contaminating other xylanases. The term dose correctly refers in particular to the objective of obtaining consistent and constant results, and the capability of optimizing dosage based upon the desired effect.

For the use in animal feed, however, the xylanase need not be that pure; it may, e.g., include other enzymes, in which case it could be termed a xylanase preparation.

The xylanase preparation can be (a) added directly to the feed, or (b) it can be used in the production of one or more intermediate compositions such as feed additives or premixes that is subsequently added to the feed (or used in a treatment process). The degree of purity described above refers to the purity of the original xylanase preparation, whether used according to (a) or (b) above.

Methods for Improving the Nutritional Value of Animal Feed

The present invention further relates to a method for improving the nutritional value of an animal feed comprising plant based material from the sub-family Panicoideae, comprising adding to the feed a xylanase variant.

The term improving the nutritional value of an animal feed means improving the availability of nutrients in the feed. The nutritional values refers in particular to improving the solubilization and degradation of the arabinoxylan-containing fraction (e.g., such as hemicellulose) of the feed, thereby leading to increased release of nutrients from cells in the endosperm that have cell walls composed of highly recalcitrant hemicellulose. Consequently, an increased release of arabinoxylan oligomers indicates a disruption of the cell walls and as a result the nutritional value of the feed is improved resulting in increased growth rate and/or weight gain and/or feed conversion (i.e., the weight of ingested feed relative to weight gain). In addition the arabinoxylan oligomer release may result in improved utilization of these components per se either directly or by bacterial fermentation in the hind gut thereby resulting in a production of short chain fatty acids that may be readily absorbed in the hind and utilised in the energy metabolism.

Methods of Improving Animal Performance

The invention further relates to a method of improving one or more performance parameters of an animal, comprising administering to one or more animals a xylanase variant and plant based material from the sub-family Panicoideae.

The plant based material from the sub-family Panicoideae may be administered together or separately with the xylanase variant. The xylanase variant may be administered in a composition or in an animal feed additive. In an embodiment, the plant based material from the sub-family Panicoideae is maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof. In a further embodiment, the the plant based material from the sub-family Panicoideae is from the seed fraction (such as endosperm and/or husk) of the plant.

In an embodiment, the improvement in the performance of an animal is an increase in body weight gain. In another embodiment, the improvement is an improved feed conversion ratio. In a further embodiment, the improvement is an increased feed efficiency. In a further embodiment, the improvement is an increase in body weight gain and/or an improved feed conversion ratio and/or an increased feed efficiency.

Methods of Solubilizing Xylan from Plant Based Materials

The invention further relates to methods of solubilizing xylan from a plant based material, e.g., by degrading the xylose backbone of sterically hindered arabinoxylan found in plant based material from the sub-family Panicoideae, thereby solubilizing increased amounts of arabinoxylan which is measured as arabinose and xylose. Increased degradation, and thereby increased arabinose and xylose release, can result in advantages for many industries which use plant based material from the sub-family Panicoideae.

The amount of starch present in untreated plant material makes it difficult to detect significant solubilization of arabinoxylan. Thus model substrates, wherein the starch and fat present in the plant material is removed without effecting the degree of substitution, can be used to aid the determination of improved enzyme combinations over known prior art combinations. One model substrate is defatted destarched maize (DFDSM) and can be prepared as described in the Examples. It is important that the model substrate is not prepared using strongly acidic or basic conditions or high temperatures, since such conditions can remove the side chain carbohydrate molecules and/or ester groups present on the xylan backbone. If these side chain groups are removed, then the complexity and degree of substitution will be reduced resulting in an arabinoxylan material which is easy to degrade by known solutions. It is for this reason that heat, acid and/or base pre-treatment is used in biomass conversion.

In order to measure the solubilization of the arabinoxylan, the soluble arabinoxylan is hydrolyzed with acid resulting in xylose and arabinose being released into the supernatant. This xylose and arabinose is then detected using, e.g., the HPLC method as described herein. The higher the degree of solubilization of the arabinoxylan, the higher the amount of xylose and arabinose released upon acid hydrolysis. It is believed that increasing the solubilization of the arabinoxylan opens up the cell walls that can result in the nutrients, such as starch and protein, which are trapped inside being released. The release of starch and other nutrients can result in improved animal performance and/or improve the nutritional value of an animal feed.

In an embodiment, the percentage solubilized xylan is at least 4% when the method is performed under the reaction conditions 20 μg xylanase variant per gram defatted destarched maize (DFDSM) and incubation at 40° C., pH 5 for 2.5 hours.

In another embodiment, the xylanase variant solubilizes at least 7% solubilized xylan from plant based material from the sub-family Panicoideae when the method is performed under the reaction conditions 20 μg xylanase variant per gram defatted destarched maize (DFDSM) and incubation at 40° C., pH 5 for 2.5 hours.

In a more preferred embodiment, the xylanase variant solubilizes at least 9.5% solubilized xylan from plant based material from the sub-family Panicoideae when the method is performed under the reaction conditions 20 μg xylanase variant per gram defatted destarched maize (DFDSM) and incubation at 40° C., pH 5 for 2.5 hours.

Methods of Releasing Starch

The invention further relates to a method of releasing starch from plant based material, comprising treating plant based material from the sub-family Panicoideae with a xylanase variant.

Processes for Producing Fermentation Products

Processes for Producing Fermentation Products from Un-Gelatinized Starch-Containing Material The invention also relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a variant protease of the invention. Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;
wherein step (i) is carried out using at least a glucoamylase and a xylanase variant of the invention.

In one embodiment, an alpha amylase, in particular, a fungal alpha-amylase, is also added in step (i). Steps (i) and (ii) may be performed simultaneously.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase;

(b) saccharifying the liquefied material obtained in step (a) using a carbohydrate-source generating enzyme;

(c) fermenting using a fermenting organism;
wherein a xylanase variant of the invention is present during step a), b) and/or c).

The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at a pH of 4-6, in particular, at a pH of 4.5-5.5, and alpha-amylase variant, optionally together with a pullulanase and/or protease, preferably metalloprotease, are added to initiate liquefaction (thinning). The liquefaction process is usually carried out at a pH of 4-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., in particular 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, *sorghum*, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment, the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an embodiment, the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular, *Pichia stipitis* such as *Pichia stipitis* CBS 5773 or *Pichia pastoris*; strains of *Candida*, in particular, *Candida arabinofermentans, Candida boidinii, Candida diddensii, Candida shehatae, Candida sonorensis, Candida tropicalis*, or *Candida utilis*. Other fermenting organisms include strains of *Hansenula*, in particular, *Hansenula anomala* or *Hansenula polymorpha*; strains of *Kluyveromyces*, in particular, *Kluyveromyces fragilis* or *Kluyveromyces marxianus*; and strains of *Schizosaccharomyces*, in particular *Schizosaccharomyces pombe*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Use in Baking

The invention discloses a method for preparing a dough which comprises incorporating into the dough a xylanase variant of the invention.

The phrase "incorporating into the dough" is defined herein as adding the xylanase variant to the dough, to any ingredient from which the dough is to be made, and/or to any mixture of dough ingredients from which the dough is to be made.

In other words, the xylanase variant may be added in any step of the dough preparation and may be added in one, two, or more steps. The xylanase variant may be added to the ingredients of dough that is kneaded and baked, using methods well known in the art.

The term "dough" is defined herein as a mixture of flour and other ingredients firm enough to knead or roll.

The dough may comprise flour derived from any cereal grain, including wheat, barley, rye, oat, corn, *sorghum*, rice, millet, and any mixtures thereof.

The dough may also comprise other conventional dough ingredients, e.g., proteins, such as milk powder, gluten, and soy; eggs (either whole eggs, egg yolks, or egg whites); an oxidant such as ascorbic acid, potassium bromate, potassium iodate, azodicarbonamide (ADA) or ammonium persulfate; an amino acid such as L-cysteine; a starch; and/or a salt such as sodium chloride, calcium acetate, sodium sulfate or calcium sulfate. The starch may be wheat starch, corn starch, maize starch, tapioca starch, cassava starch, potato starch; and/or a sugar such as sucrose, cane sugar, lactose, or high fructose corn syrup.

The dough may comprise fat (triglyceride) such as granulated fat or shortening.

The dough may be fresh, frozen, or par-baked (pre-baked).

The dough is normally leavened dough or dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g., a commercially available strain of *S. cerevisiae*.

Baked Product

The present invention also relates to a process of preparing a baked or steamed product from the dough (such as fiber dough), either of a soft or a crisp character and of a white, light or dark type.

Examples of baked products are bread typically in the form of loaves or rolls, pan bread, toast bread, pan bread with and without lid, buns, hamburger buns, rolls, baguettes, brown bread, whole meal bread, rich bread, bran bread, flat bread, tortilla, pita, Arabic bread, Indian flat bread, steamed bread, and any variety thereof.

Preferred Embodiments of the Invention

Preferred embodiments of the invention are described in the set of items below.

1. A xylanase variant, comprising a substitution at one or more positions corresponding to positions 24, 26, 36, 37, 60, 71, 74, 75, 76, 124, 133, 155, 167, 208, 317, and 321 of SEQ ID NO: 1, wherein the xylanase variant has xylanase activity and wherein the xylanase variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1, 2, 3, 4, 5 or 6.

2. The xylanase variant of item 1, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 1.

3. The xylanase variant of item 1 or 2, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 2.

4. The xylanase variant of any of items 1 to 3, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 3.

5. The xylanase variant of any of items 1 to 4, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 4.

6. The xylanase variant of any of items 1 to 5, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 5.

7. The xylanase variant of any of items 1 to 6, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to SEQ ID NO: 6.

8. The xylanase variant of any of items 1 to 7, wherein the variant has been isolated.

9. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 1.

10. The xylanase variant of item 9, wherein the parent xylanase comprises or consists of the amino acid sequence of SEQ ID NO: 1 or is a fragment of SEQ ID NO: 1, wherein the fragment has xylanase activity.

11. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2.

12. The xylanase variant of item 11, wherein the parent xylanase comprises or consists of the amino acid sequence of SEQ ID NO: 2 or is a fragment of SEQ ID NO: 2, wherein the fragment has xylanase activity.

13. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 3.

14. The xylanase variant of item 13, wherein the parent xylanase comprises or consists of the amino acid sequence of SEQ ID NO: 3 or is a fragment of SEQ ID NO: 3, wherein the fragment has xylanase activity.

15. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 4.

16. The xylanase variant of item 15, wherein the parent xylanase comprises or consists of the amino acid sequence of SEQ ID NO: 4 or is a fragment of SEQ ID NO: 4, wherein the fragment has xylanase activity.

17. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 5.

18. The xylanase variant of item 17, wherein the parent xylanase comprises or consists of the amino acid sequence of SEQ ID NO: 5 or is a fragment of SEQ ID NO: 5, wherein the fragment has xylanase activity.

19. The xylanase variant of any of items 1 to 8, which is a variant of a parent xylanase wherein the parent xylanase has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 6.

20. The xylanase variant of item 19, wherein the parent xylanase comprises or consists of the amino acid sequence of SEQ ID NO: 6 or is a fragment of SEQ ID NO: 6, wherein the fragment has xylanase activity.

21. The xylanase variant of any of items 1 to 20, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent xylanase.

22. The xylanase variant of any of items 1 to 21, wherein the parent xylanase is obtained or obtainable from the taxonomic order Bacillales, preferably the taxonimic family Bacillaceae.

23. The xylanase variant of any of items 1 to 22, wherein the parent xylanase is obtained or obtainable from the taxonomic genus *Bacillus subtilis, Bacillus amyloliquefaciens, Bacillus licheniformis* or *Paenibacillus pabuli*.

24. The xylanase variant of any of items 1 to 20, wherein the number of alterations is 1-20, e.g., 1-10 and 1-5, such as 1, 2, 3, 4, 5, 6, 7, 8, 9 or 10 alterations.

25. The xylanase variant of any of items 1 to 24, which comprises a substitution at a position corresponding to position 24.

26. The xylanase variant of item 25, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Trp.

27. The xylanase variant of any of items 1 to 26, which comprises a substitution at a position corresponding to position 26.

28. The xylanase variant of item 27, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Glu.

29. The xylanase variant of any of items 1 to 28, which comprises a substitution at a position corresponding to position 36.

30. The xylanase variant of item 29, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Leu or Thr.

31. The xylanase variant of any of items 1 to 30, which comprises a substitution at a position corresponding to position 37.

32. The xylanase variant of item 31, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Leu or Thr.

33. The xylanase variant of any of items 1 to 32, which comprises a substitution at a position corresponding to position 60.

34. The xylanase variant of item 33, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Asn.

35. The xylanase variant of any of items 1 to 34, which comprises a substitution at a position corresponding to position 71.

36. The xylanase variant of item 35, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Ile, Leu, or Thr.

37. The xylanase variant of any of items 1 to 36, which comprises a substitution at a position corresponding to position 74.

38. The xylanase variant of item 37, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Ile or Leu.

39. The xylanase variant of any of items 1 to 38, which comprises a substitution at a position corresponding to position 75.

40. The xylanase variant of item 39, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Asn, Glu, Leu, or Thr.

41. The xylanase variant of any of items 1 to 40, which comprises a substitution at a position corresponding to position 76.

42. The xylanase variant of item 41, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Leu.

43. The xylanase variant of any of items 1 to 42, which comprises a substitution at a position corresponding to position 124.

44. The xylanase variant of item 43, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Tyr.

45. The xylanase variant of any of items 1 to 44, which comprises a substitution at a position corresponding to position 133.

46. The xylanase variant of item 45, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Ile.

47. The xylanase variant of any of items 1 to 46, which comprises a substitution at a position corresponding to position 155.

48. The xylanase variant of item 47, wherein the substitution is with Ala, Arg, Asn, Asp, Cys, Gln, Glu, Gly, His, Ile Leu, Lys, Met, Phe, Pro, Ser, Thr, Trp, Tyr, or Val, in particular, with Met.

49. The xylanase variant of any of items 1 to 48, which comprises a substitution at a position corresponding to position 167.

50. The xylanase variant of item 49, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Glu.

51. The xylanase variant of any of items 1 to 50, which comprises a substitution at a position corresponding to position 208.

52. The xylanase variant of item 51, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Leu.

53. The xylanase variant of any of items 1 to 52, which comprises a substitution at a position corresponding to position 317.

54. The xylanase variant of item 53, wherein the substitution is with Ala, Arg, Asn, Asp, Cys, Gln, Glu, Gly, His, Ile, Leu, Lys, Met, Phe, Pro, Ser, Thr, Trp, Tyr, or Val, in particular, with Asp.

55. The xylanase variant of any of items 1 to 54, which comprises a substitution at a position corresponding to position 321.

56. The xylanase variant of item 55, wherein the substitution with Ala, Arg, Asn, Asp, Cys, Gln, Glu, Gly, His, Ile, Leu, Lys, Met, Phe, Pro, Ser, Thr, Trp, Tyr, or Val, in particular, with Ala.

57. The xylanase variant of any of items 1 to 56, which comprises a substitution at two of the positions corresponding to positions 24, 26, 36, 37, 71, 74, 75, 76, 155, and 208.

58. The xylanase variant of any of items 1 to 56, which comprises a substitution at three of the positions corresponding to positions 24, 26, 36, 37, 71, 74, 75, 76, 155, and 208.

59. The xylanase variant of any of items 1 to 56, which comprises a substitution at four of the positions corresponding to positions 24, 26, 36, 37, 71, 74, 75, 76, 155, and 208.

60. The xylanase variant of any of items 1 to 56, which comprises a substitution at five of the positions corresponding to positions 24, 26, 36, 37, 71, 74, 75, 76, 155, and 208.

61. The xylanase variant of any of items 1 to 56, which comprises a substitution at six of the positions corresponding positions 24, 26, 36, 37, 71, 74, 75, 76, 155, and 208.

62. The xylanase variant of any of items 1 to 56, which comprises a substitution at seven of the positions corresponding positions 24, 26, 36, 37, 71, 74, 75, 76, 155, and 208.

63. The xylanase variant of any of items 1 to 56, which comprises a substitution at each position corresponding to positions 24, 26, 36, 37, 71, 74, 75, 76, 155, and 208.

64. The xylanase variant of any of items 1 to 63, which has an improved property relative to the parent, wherein the improved property is selected from the group consisting of catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability.

65. The xylanase variant of item 64, wherein the parent xylanase is SEQ ID NO: 1.

66. The xylanase variant of any of items 1 to 63, which has improved thermostability relative to the parent xylanase.

67. The xylanase variant of any of items 1 to 63, which has improved thermostability relative to SEQ ID NO: 1.

68. A composition comprising the xylanase variant of any of items 1 to 67 and a formulating agent.

69. The composition of item 68, wherein the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose.

70. The composition of item 68 or 69, further comprising one or more additional enzymes.

71. The composition of item 70, wherein the one or more additional enzymes is selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, glucan 1,4-α-glucosidase, glucan 1,4-alpha-maltohydrolase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase, or any combination thereof.

72. The composition of any of items 68 to 71, further comprising one or more microbes.

73. The composition of item 72, wherein the one or more microbes is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococcus acidilactici*, *Pediococcus* sp., *Propionibacterium thoenii*, *Propionibacterium* sp. and *Streptococcus* sp. or any combination thereof.

74. The composition of any of items 68 to 73, further comprising plant based material.

75. The composition of item 74, wherein the plant based material is from the sub-family Panicoideae 76. The composition of item 75, wherein the plant based material from the sub-family Panicoideae is maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof.

77. The composition of item 74 to 75, wherein the plant based material from the sub-family Panicoideae is from the seed fraction (such as endosperm and/or husk) of the plant.

78. A granule comprising the xylanase variant of any of items 1 to 67 and a formulating agent.

79. The granule of item 78, wherein the one or more formulating agents is selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1, 2-propylene glycol, 1, 3-propylene glycol, sodium sulfate, dextrin, cellulose, sodium thiosulfate, kaolin and calcium carbonate.

80. The granule of item 78 or 79, wherein the granule comprises a core particle and one or more coatings.

81. The granule of item 80, wherein the coating comprises salt and/or wax and/or flour.

82. The granule of any of items 78 to 81, further comprising one or more additional enzymes.

83. The granule of item 82, wherein the one or more additional enzymes is selected from the group consisting of acetyl xylan esterase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lipase, glucan 1,4-α-glucosidase, glucan 1,4-alpha-maltohydrolase, lysophospholipase, lysozyme, mannanase, alpha-mannosidase, beta-mannosidase, phytase, phospholipase A1, phospholipase A2, phospholipase C, phospholipase D, protease, pullulanase, pectinase, pectin lyase, xylanase, beta-xylosidase, or any combination thereof.

84. An animal feed additive comprising the xylanase variant of any of items 1 to 67, the composition of any of items 68 to 77 or the granule of any of items 78 to 83 and one or more components selected from the group consisting of:
  one or more vitamins;
  one or more minerals;
  one or more amino acids;
  one or more phytogenics;
  one or more prebiotics;
  one or more organic acids; and
  one or more other feed ingredients.

85. A liquid formulation comprising the xylanase variant of any of items 1 to 67.

86. The liquid formulation of item 85, wherein the xylanase variant is dosed between 0.01% to 25% w/w of liquid formulation, preferably 0.05% to 20% w/w, more preferably 0.2% to 15% w/w, more preferably 0.5% to 15% w/w or most preferably 1.0% to 10% w/w xylanase variant.

87. The liquid formulation of item 85 or 86, wherein the formulation further comprises 20% to 80% w/w of polyol.

88. The liquid formulation of item 87, wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600 or any combination thereof.

89. The liquid formulation of any of items 85 to 88, wherein the formulation further comprises 0.01% to 2.0% w/w preservative.

90. The liquid formulation of item 89, wherein the preservative is selected from the group consisting of sodium sorbate, potassium sorbate, sodium benzoate and potassion benzoate or any combination thereof.

91. The liquid formulation of any of items 85 to 90, further comprising one or more components selected from the list consisting of:
  one or more enzymes;
  one or more microbes;
  one or more vitamins;
  one or more minerals;
  one or more amino acids;
  one or more phytogenics;
  one or more prebiotics;
  one or more organic acids; and
  one or more other feed ingredients.

92. A method of preparing an animal feed comprising applying the liquid formulation of any of items 85 to 91 onto plant based material.

93. The method of item 92, wherein the liquid formulation is applied via a spray.

94. The method of item 92 or 93, wherein the plant based material comprises legumes, cereals, oats, rye, barley, wheat, maize, corn, *sorghum*, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

95. The method of any of items 92 to 94, wherein the plant based material is in pelleted form.

96. An animal feed comprising the xylanase variant of any of items 1 to 67, the composition of any of items 68 to 77, the granule of any of items 78 to 83, the animal feed additive of item 84 or the liquid formulation of any of items 85 to 91 and plant based material.

97. The animal feed of item 96, wherein the plant based material is from the sub-family Panicoideae.

98. The animal feed of item 97, wherein the plant based material from the sub-family Panicoideae is maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof.

99. The animal feed of item 96 or 97, wherein the plant based material from the sub-family Panicoideae is from the seed fraction (such as endosperm and/or husk) of the plant.

100. A pelleted animal feed prepared using the method of any of items 92 to 95 or by pelleting the animal feed of any of items 96 to 99.

101. A method of improving one or more performance parameters of an animal comprising administering to one or more animals the xylanase variant of any of items 1 to 67, the composition of any of items 68 to 77, the granule of any of items 78 to 83, the animal feed additive of item 84, the liquid formulation of any of items 85 to 91, the animal feed of any of items 96 to 99 or the pelleted animal feed of item 100.

102. A method of solubilizing xylan from plant based material, comprising treating plant based material with the xylanase variant of any of items 1 to 67, the composition of any of items 68 to 77, the granule of any of items 78 to 83, the animal feed additive of item 84 or the liquid formulation of any of items 85 to 91.

103. A method of releasing starch from plant based material, comprising treating plant based material with the xylanase variant of any of items 1 to 67, the composition of any of items 68 to 77, the granule of any of items 78 to 83, the animal feed additive of item 84 or the liquid formulation of any of items 85 to 91.

104. A method for improving the nutritional value of an animal feed, comprising adding to the feed comprising plant based material the xylanase variant of any of items 1 to 67, the composition of any of items 68 to 77, the granule of any of items 78 to 83, the animal feed additive of item 84 or the liquid formulation of any of items 85 to 91.

105. The method of any of items 102 to 104, wherein the plant based material is from the sub-family Panicoideae.

106. The method of item 105, wherein the plant based material from the sub-family Panicoideae is maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof.

107. The method of item 105 or 106, wherein the plant based material from the sub-family Panicoideae is from the seed fraction (such as endosperm and/or husk) of the plant.

108. Use of the xylanase variant of any of items 1 to 67, the composition of any of items 68 to 77, the granule of any of items 78 to 83, the animal feed additive of item 84, the liquid formulation of any of items 85 to 91, the animal feed of any of items 96 to 99 or the pelleted animal feed of item 100:
   in animal feed;
   in animal feed additives;
   in the preparation of a composition for use in animal feed;
   for improving the nutritional value of an animal feed;
   for increasing digestibility of an animal feed;
   for improving one or more performance parameters in an animal;
   for solubilizing xylan from plant based material
   for releasing starch from plant based material.

109. The use of item 108, wherein the plant based material is from the sub-family Panicoideae.

110. The use of item 109, wherein the plant based material from the sub-family Panicoideae is maize, corn, *sorghum*, switchgrass, millet, pearl millet, foxtail millet or in a processed form such as milled corn, milled maize, defatted maize, defatted destarched maize, milled *sorghum*, milled switchgrass, milled millet, milled foxtail millet, milled pearl millet, or any combination thereof.

111. The use of any of items 108 to 110, wherein the plant based material from the sub-family Panicoideae is from the seed fraction (such as endosperm and/or husk) of the plant.

112. A process of producing a fermentation product, comprising the following steps:
   (a) saccharifying a starch-containing material at a temperature below the initial gelatinization temperature with an alpha-amylase, a glucoamylase, and a xylanase variant of any of items 1 to 67; and
   (b) fermenting using a fermentation organism.

113. A process for producing a fermentation product from starch-containing material comprising the steps of:
   (a) liquefying a starch-containing material with an alpha-amylase;
   (b) saccharifying the liquefied material obtained in step (a) with a glucoamylase and a xylanase variant of any of items 1 to 67;
   (c) fermenting using a fermenting organism.

114. The process of item 113, wherein steps b) and c) are performed simultaneously.

115. The process of any of items 112 to 114, wherein the starch containing material comprises maize, corn, wheat, rye, barley, triticale, *sorghum*, switchgrass, millet, pearl millet, foxtail millet.

116. The process of any of items 112 to 115, wherein the fermentation product is an alcohol, particularly ethanol.

117. The process of any of items 112 to 116 wherein the fermenting organism is yeast, particularly *Saccharomyces* sp., more particularly *Saccharomyces cerevisiae*.

118. The use of a xylanase variant of any of items 1 to 67 for producing ethanol from a starch containing material.

119. A method for preparing a dough or a baked product prepared from the dough which method comprises incorporating into the dough a xylanase variant of any of items 1 to 67.

120. The method of item 119, wherein the dough comprises flour selected from the group consisting of wheat, barley, rye, oat, corn, *sorghum*, rice, millet, and any mixtures thereof.

121. An isolated polynucleotide encoding the xylanase variant of any of items 1 to 67, wherein the polynucleotide is operably linked to one or more control sequences that direct the production of the xylanase variant in a recombinant host cell.

122. A nucleic acid construct comprising the polynucleotide of item 121.

123. An expression vector comprising the polynucleotide of item 121.

124. A recombinant host cell comprising a nucleic acid construct of item 122 or expression vector of item 123.

125. A method of producing a xylanase variant, comprising:
   a. cultivating the host cell of item 124 under conditions suitable for expression of the xylanase variant; and
   b. recovering the xylanase variant.

126. A transgenic plant, plant part or plant cell transformed with the polynucleotide of item 121.

127. A method of producing a xylanase variant of any of items 1 to 67, comprising:
   a. cultivating a transgenic plant or a plant cell comprising a polynucleotide encoding the xylanase variant under conditions conducive for production of the xylanase variant; and
   b. recovering the xylanase variant.

128. A polynucleotide encoding the xylanase variant of any of items 1 to 67.

129. A nucleic acid construct or expression vector comprising the polynucleotide of item 128 operably linked to one or more control sequences that direct the production of the polypeptide in an expression host.

130. A recombinant host cell comprising the polynucleotide of item 128 operably linked to one or more control sequences that direct the production of the polypeptide.

131. A method of producing the xylanase variant of any of items 1 to 67, comprising:
   (a) cultivating a cell, which in its wild-type form produces the polypeptide, under conditions conductive for production of the polypeptide; and
   (b) recovering the polypeptide.

132. A method of producing the xylanase variant of any of items 1 to 67, comprising:
   (a) cultivating the recombinant host cell of item 130 under conditions conductive for production of the polypeptide; and
   (b) recovering the polypeptide.

133. A whole broth formulation or cell culture composition comprising the xylanase variant of any of items 1 to 67.

134. A method for obtaining a xylanase variant, comprising introducing into a parent xylanase a substitution at one or more positions corresponding to positions 24, 26, 36, 37, 60, 71, 74, 75, 76, 124, 133, 155, 167, 208, 317, and 321 of SEQ ID NO: 1, wherein the xylanase variant has xylanase activity; and recovering the xylanase variant.

135. The method of item 134, wherein the xylanase variant has an improved property relative to the parent, wherein the improved property is selected from the group consisting of catalytic efficiency, catalytic rate, chemical stability, oxidation stability, pH activity, pH stability, specific activity, stability under storage conditions, substrate binding, substrate cleavage, substrate specificity, substrate stability, surface properties, thermal activity, and thermostability.

136. The method of any of items 134 to 135, wherein the parent xylanase has at least 70% identity, preferably at least 80%, more preferably at least 85%, even more preferably at least 90%, or most preferably at least 95% identity to SEQ ID NO: 1.

137. The method of any of items 134 to 136, wherein the substitution is selected from the group consisting of H24W, A26E, R36L, R36T, E37T, R60N, K71T, K71I, V74L, V74I, K75N, K75L, H76L, I155M, N167E, V208L, S317D and G321A.

138. A xylanase variant produced by the method of any of items 134 to 137.

The present invention is further described by the following examples that should not be construed as limiting the scope of the invention.

EXAMPLES

Substrates

Preparation of Destarched Maize (DSM)

107 kg of milled maize (<10 mm) is mixed in a tank with 253 kg of tap water at 53° C. to make a slurry. The temperature of the slurry is 47° C. and the pH 5.9. The pH is adjusted to 6.15 with 1 L of 1 N NaOH and the tank is then heated to 95° C. 1.119 kg of Termamyl® alpha-amylase (Novozymes A/S, Bagsvaerd, Denmark) is added at 52° C. and incubated for 80 minutes at 95° C. The pH measured at the end of the incubation is 6.17. Cold tap water is added to the slurry and the slurry is centrifuged and decanted 3 times using a Westfalia decanter CA-225-110 (4950±10 rpm, flow ~600 l/h) giving 64.5 kg of sludge. The sludge is then collected, frozen and freeze-dried to give 17.1 kg of destarched maize (DSM).

Preparation of Defatted Destarched Maize (DFDSM)

500 mL acetone is added to 100 grams of destarched maize, prepared as described above. The slurry is stirred for 5 minutes and allowed to settle. The acetone is decanted and the procedure repeated 2 times. The residue is air dried overnight to give defatted destarched maize (DFDSM) which is stored at room temperature.

Preparation of Destarched *Sorghum*

Whole *sorghum* seeds are milled and sieved and a fraction below 0.5 mm is used for further processing. The sieved fraction is suspended in 25 mM NaOAc pH 5.5 at 20% dry matter and destarched. The destarching involves a first step at 85° C. with 500 ppm Termamyl SC alpha-amylase (Novozymes A/S, Bagsvaerd, Denmark) for 20 min followed by an overnight incubation using 250 ppm Attenuzyme Flex (Novozymes A/S, Bagsvaerd, Denmark) at 65° C. The slurry is centrifuged and the liquid decanted. After this another destarching is made using by adding MilliQ water and 200 ppm Termamyl SC and 200 ppm Attenuzyme Flex and incubating overnight at 65° C.

The *sorghum* fiber is separated from the liquid by vacuum filtration through a Whatman F glass fiber filter. The filter cake is then washed several times with excess of water to remove soluble sugars. Finally, the destarched *sorghum* fiber was dried in an oven at 65° C. and the dry fiber milled quickly in a coffee grinder so that the particle size is in general less than 1 mm.

Xylose Solubilization Assay

The activity of a xylanase variant towards defatted destrached Maize (DFDSM) is measured by High-Performance Anion-Exchange Chromatography with Pulsed Amperometric Detection (HPAE-PAD). 2% (w/w) DFDSM suspension is prepared in 100 mM sodium acetate, 5 mM $CaCl_2$, pH 5 and allowed to hydrate for 30 minutes at room temperature under gently stirring. After hydration, 200 µl substrate suspension was pipetted into a 96 well plate and mixed with 20 µl enzyme solution to obtain a final enzyme concentration of 20 PPM relative to substrate (20 µg enzyme/g substrate). The enzyme/substrate mixtures are left for hydrolysis in 2.5 hours at 40° C. under gently agitation (500 RPM) in a plate incubator (Biosan PST-100 HL). After enzymatic hydrolysis, the enzyme/substrate plates are centrifuged for 10 minutes at 3000 RPM and 50 µl supernatant (hydrolysate) is mixed with 100 µl 1.6 M HCl and transferred to 300 µl PCR tubes and left for acid hydrolysis for 40 minutes at 90° C. in a PCR machine. The purpose of the acid hydrolysis is to convert soluble polysaccharides, released by the xylanase variant, into mono-saccharides, which can be quantified using HPAE-PAD. Samples are neutralized with 125 µl 1.4 M NaOH after acid hydrolysis and mounted on the HPAE-PAD for mono-saccharide analysis (xylose, arabinose and glucose) (Dionex ICS-3000 using a CarboPac PA1 column). Appropriate calibration curves are made using mono-saccharides stock solutions which are subjected to the same procedure of acid hydrolysis as the samples. The percentage xylose solubilized is calculated according to the equation:

$$\% \text{ Xylose solubilized} = \frac{[\text{Xylose}] * V * MW}{Xxyl * Msub}$$

where [xylose] denotes the concentration of xylose in the supernatant measured by HPAE-PAD, V the volume of the sample, MW, the molecular weight of internal xylose in arabinoxylan (132 g/mol), Xxyl, the fraction of xylose in DFDSM (0.102) and Msub, the mass of DFDSM in the sample.

Example 1: Construction of Variants of the Xylanase of SEQ ID NO: 1

Xylanase variants were generated by site-directed mutagenesis. Genomic DNA prepared from the organism containing the xylanase gene was used as a template for generating the site-directed mutants.

A mutagenic forward primer and a reverse primer were used to generate a fragment. This fragment was used as a megaprimer to get an insertion cassette. To enable integration by double cross-over upon transformation, the cassette contained upstream and downstream sequences at the ends. Selection was done and the mutation was confirmed by DNA sequencing of the xylanase gene.

The variants were tested as described in Example 2.

Example 2: Protein Thermal Unfolding Analysis (TSA, Thermal Shift Assay)

Protein thermal unfolding of variants of SEQ ID NO: 1 was monitored with Sypro Orange (Invitrogen, S-6650) using a real-time PCR instrument (Applied Biosystems; Step-One-Plus). Buffer: 100 mM formic acid/sodium formate pH 3.77+50 mM NaCl.

In a 96-well white PCR-plate, 15 µl sample (purified desalted enzyme @ 50 ppm in buffer) was mixed (1:1) with Sypro Orange (Conc.=10×; stock solution from supplier=5000×) in buffer.

The plate was sealed with an optical PCR seal. The PCR instrument was set at a scan-rate of 76° C. per hour, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (Gregory et al., 2009, *J. Biomol. Screen.* 14: 700). The Delta Tm is the difference between the Tm of the xylanase variant and the Tm of the wild-type xylanase and are presented in table 2 below.

TABLE 2

Protein thermal unfolding of xylanase variants of SEQ ID NO: 1

| Mutation(s) | Delta Tm (° C.) |
|---|---|
| H24W + K71L + V74L + H76L + I155M + V208L | 8.9 |
| H24W + A26E + K71L + V74L + H76L + I155M + V208L | 8.8 |
| A26E + K71L + V74L + H76L + I155M + V208L | 8.2 |
| K71L + V74L + H76L + I155M + V208L | 8.1 |
| H24W + V74L + H76L + I155M + V208L | 8.1 |
| H24W + A26E + V74L + H76L + I155M + V208L | 7.7 |
| H24W + K75L + H76L + I155M + V208L | 7.5 |
| A26E + V74L + H76L + I155M + V208L | 7.2 |
| H24W + V74L + I155M + V208L | 7.2 |
| H24W + V74L + K75L + I155M + V208L | 7.2 |
| H24W + A26E + K75L + H76L + I155M + V208L | 7.1 |
| V74L + H76L + I155M + V208L | 6.9 |
| K71L + V74L + I155M + V208L | 6.8 |
| H76L + I155M + V208L | 6.7 |
| K75L + H76L + I155M + V208L | 6.7 |
| A26E + K75L + H76L + I155M + V208L | 6.7 |
| A26E + V74L + I155M + V208L | 6.6 |
| A26E + V74L + K75L + I155M + V208L | 6.5 |
| V74L + K75L + I155M + V208L | 6.1 |
| V74L + I155M + V208L | 6.1 |
| R36T + I155M + V208L | 5.9 |
| H24W + I155M + V208L | 5.8 |
| K75L + I155M + V208L | 5.5 |
| A26E + I155M + V208L | 5.4 |
| R36L + I155M + V208L | 5.1 |
| E37T + I155M + V208L | 5.0 |
| I155M + V208L | 4.9 |
| F124Y + I155M + V208L | 4.6 |
| E37T + I155M + V208L | 4.6 |
| I155M + N167E + V208L | 4.5 |
| Y133I + I155M + V208L | 4.1 |
| H24W + V208L | 3.8 |
| A26E + V208L | 3.6 |
| H24W + I155M | 3.5 |
| R36T + I155M | 3.0 |
| A26E + I155M | 2.8 |
| H24W + V74L | 2.7 |
| K71L + V208L | 2.5 |
| I155M | 2.5 |
| V208L | 2.4 |
| R36L + I155M | 2.4 |
| A26E + V74L | 2.3 |
| I155M + N167E | 2.2 |
| R36T + V208L | 2.2 |
| H24W | 2.1 |
| R36L + V208L | 2.1 |
| N167E + V208L | 2.0 |
| K71L + H76L | 1.9 |
| E37T + V208L | 1.8 |
| A26E | 1.6 |
| K75E + H76L | 1.4 |
| H76L | 1.3 |
| K71T + K75T + H76L | 0.9 |
| K75L + H76L | 0.7 |
| S317D | 0.7 |
| V74L | 0.6 |
| R60N | 0.5 |
| V74I | 0.4 |
| G321A | 0.4 |
| K75N | 0.3 |
| K71T | 0.3 |
| K71I | 0.3 |
| R36T + E37T | 0.3 |
| K75L | 0.2 |
| Wild-type (SEQ ID NO: 1) | 0.0 |

The results show that the xylanase variants have improved thermostability relative to the wild-type xylanase.

Example 3: Protein Thermal Unfolding Analysis (TSA, Thermal Shift Assay) of Culture Broth Samples Selected substitutions were made in another GH30 subfamily 8 xylanase (using the method as described in Example 1) to see whether such substitutions would also show similar thermostabilising properties. The GH30_8 xylanase was SEQ ID NO: 6, a GH30_8 xylanase from *Bacillus amyloliquefaciens* having 90.5% identity to SEQ ID NO: 1.

Protein thermal unfolding was monitored with Sypro Orange (Invitrogen, S-6650) using a real-time PCR instrument (Applied Biosystems; Step-One-Plus).

Culture broth samples were flocculated and diluted prior to TSA analysis:

To Culture broth was added 4 v/v-% GC850™ ($Al_2(OH)_5Cl$) obtainable from Gulbrandsen or NordPac 18 (available from Nordisk Aluminat A/S, Denmark), mixed and spun down.

To the supernatant was 10 v/v-% 1.0 M HCl, followed by 8-fold dilution in buffer: 100 mM formic acid/sodium formate pH 3.77+50 mM NaCl.

In a 96-well white PCR-plate, 15 µl sample (flocculated and diluted) was mixed (1:1) with Sypro Orange (Conc.=10×; stock solution from supplier=5000×) in buffer.

The plate was sealed with an optical PCR seal. The PCR instrument was set at a scan-rate of 76° C. per hour, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (Gregory et al., 2009, *J. Biomol. Screen.* 14: 700).

The Delta Tm is the difference between the Tm of the xylanase variant and the Tm of the wild-type xylanase and are presented in table 3 below.

TABLE 3

Protein thermal unfolding of xylanase variants of SEQ ID NO: 6

| Mutation | Delta Tm (° C.) |
|---|---|
| I155M | 3.3 |
| V208L | 2.9 |
| H24W | 2.6 |
| A26E | 1.9 |
| H76L | 2.9 |
| Wild-type (SEQ ID NO: 6) | 0.0 |

The results show that the substitutions which result in thermostabilisation of SEQ ID NO: 1 also result in thermostabilisation of SEQ ID NO: 6. Therefore, it can be expected that such substitutions would result in the thermostabilisation of other similar GH30_8 xylanases, especially those GH30_8 xylanases from the taxonomic family Bacillaceae.

Example 4: Animal Feed and Animal Feed Additives

Granule

The granule is prepared by granulating a xylanase variant of the invention with a filler such as sodium sulfate, magnesium sulfate, calcium carbonate and/or cellulose and then optionally coating the granule with a wax coating (e.g., hydrogenated palm oil) or a salt coating (e.g., sodium sulfate and/or magnesium sulfate).

Alternatively, granule is prepared by absorbing a liquid solution of a xylanase variant of the invention onto an inert core and then optionally coating the granule with a wax coating (e.g., hydrogenated palm oil) or a salt coating (e.g., sodium sulfate and/or magnesium sulfate).

Animal Feed Additive

A premix formulation of a xylanase variant of the invention containing 0.01 g to 10 g enzyme protein per kilo of premix (optionally formulated as a coated granule) is added to the following premix:

| 5000000 | IE | Vitamin A |
|---|---|---|
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:
- 62.55% Maize
- 33.8% Soybean meal (50% crude protein)
- 1.0% Soybean oil
- 0.2% DL-Methionine
- 0.22% DCP (dicalcium phosphate)
- 0.76% $CaCO_3$ (calcium carbonate)
- 0.32% Sand
- 0.15% NaCl (sodium chloride)
- 1% of the above Premix The ingredients are mixed, and the feed is pelleted at the desired temperature, e.g., 60, 65, 75, 80, 85, 90 or even 95° C.

Liquid Formulation

A liquid formulation of a xylanase variant of the invention comprises 0.1% to 10 w/w enzyme protein, 40-60% glycerol, 0.1 to 0.5% sodium benzoate and water. The liquid formulation is sprayed onto the pelleted animal feed described above (in this case the animal feed additive would not include the xylanase variant of the invention present).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A xylanase variant, comprising a substitution at a position corresponding to position 74 of SEQ ID NO: 1, wherein the xylanase variant has xylanase activity and wherein the xylanase variant has at least 97% and less than 100% sequence identity to SEQ ID NO: 1, 2, 3, 4, 5 and/or 6.

2. The xylanase variant of claim 1, which has at least 98% and less than 100% sequence identity to SEQ ID NO: 1.

3. The xylanase variant of claim 1, wherein the substitution is 74I.

4. The xylanase variant of claim 1, further comprising a substitution at a position corresponding to position 24, 26, 36, 37, 60, 71, 75, 76, 124, 133, 155, 167, 208, 317, and 321 of SEQ ID NO: 1.

5. The xylanase variant of claim 4, wherein the substitution is selected from the group consisting of 24W, 26E, 36L, 36T, 37T, 60N, 71T, 71I, 75N, 75L, 76L, 155M, 167E, 208L, 317D and 321A.

6. A composition comprising the xylanase variant of claim 1 and a formulating agent.

7. A granule comprising the xylanase variant of claim 1.

8. An animal feed additive comprising the xylanase variant of claim 1 and one or more components selected from the group consisting of:
one or more vitamins;
one or more minerals;
one or more amino acids;
one or more phytogenics;
one or more prebiotics;
one or more organic acids; and
one or more other feed ingredients.

9. A liquid formulation comprising the xylanase variant of claim 1 and 20-80% w/w of polyol.

10. An animal feed comprising the xylanase variant of claim 1 and plant-based material.

11. A method of improving one or more performance parameters of an animal comprising administering to the animal the xylanase variant of claim 1.

12. A method of solubilizing xylan from a plant-based material, comprising treating the plant-based material with the xylanase variant of claim 1.

13. A polynucleotide encoding the xylanase variant of claim 1, wherein the polynucleotide is operably linked to one or more control sequences that direct the production of the xylanase variant in a recombinant host cell.

14. A recombinant host cell comprising a polynucleotide of claim 13.

15. A method of producing a xylanase variant, comprising:
(a) cultivating the host cell of claim 14 under conditions suitable for expression of the xylanase variant; and
(b) recovering the xylanase variant.

16. A xylanase variant, comprising a substitution at a position corresponding to position 74 of SEQ ID NO: 1 with leucine, wherein the xylanase variant has xylanase activity and wherein the xylanase variant has at least 90% and less than 100% sequence identity to SEQ ID NO: 1, 2, 3, 4, 5 and/or 6.

17. The xylanase variant of claim 16, which has at least 95% and less than 100% sequence identity to SEQ ID NO: 1.

18. The xylanase variant of claim 16, further comprising a substitution at a position corresponding to position 24, 26, 36, 37, 60, 71, 75, 76, 124, 133, 155, 167, 208, 317, and 321 of SEQ ID NO: 1.

19. The xylanase variant of claim 18, wherein the substitution is selected from the group consisting of 24W, 26E, 36L, 36T, 37T, 60N, 71T, 71I, 75N, 75L, 76L, 155M, 167E, 208L, 317D and 321A.

20. A composition comprising the xylanase variant of claim 16 and a formulating agent.

21. A granule comprising the xylanase variant of claim 16.

22. An animal feed additive comprising the xylanase variant of claim 16 and one or more components selected from the group consisting of:
one or more vitamins;
one or more minerals;
one or more amino acids;
one or more phytogenics;
one or more prebiotics;
one or more organic acids; and
one or more other feed ingredients.

23. A liquid formulation comprising the xylanase variant of claim 16 and 20-80% w/w of polyol.

24. An animal feed comprising the xylanase variant of claim 16 and plant-based material.

25. A method of improving one or more performance parameters of an animal comprising administering to the animal the xylanase variant of claim 16.

26. A method of solubilizing xylan from a plant-based material, comprising treating the plant-based material with the xylanase variant of claim 16.

27. A polynucleotide encoding the xylanase variant of claim 16, wherein the polynucleotide is operably linked to one or more control sequences that direct the production of the xylanase variant in a recombinant host cell.

28. A recombinant host cell comprising a polynucleotide of claim 27.

29. A method of producing a xylanase variant, comprising:
   (a) cultivating the host cell of claim 28 under conditions suitable for expression of the xylanase variant; and
   (b) recovering the xylanase variant.

\* \* \* \* \*